US012777294B2

(12) United States Patent
Vandali et al.

(10) Patent No.: US 12,777,294 B2
(45) Date of Patent: Oct. 27, 2026

(54) PITCH CODING ENHANCEMENT FOR HEARING DEVICES

(71) Applicant: Cochlear Limited, Macquarie University (AU)

(72) Inventors: Andrew E Vandali, Greenvale (AU); Zachary Mark Smith, Pymble (AU)

(73) Assignee: Cochlear Limited, Macquarie University (AU)

( * ) Notice: Subject to any disclaimer, the term of this patent is extended or adjusted under 35 U.S.C. 154(b) by 183 days.

(21) Appl. No.: 18/559,417

(22) PCT Filed: Apr. 20, 2022

(86) PCT No.: PCT/IB2022/053692
§ 371 (c)(1),
(2) Date: Nov. 7, 2023

(87) PCT Pub. No.: WO2022/238791
PCT Pub. Date: Nov. 17, 2022

(65) Prior Publication Data

US 2024/0244383 A1 Jul. 18, 2024

Related U.S. Application Data

(60) Provisional application No. 63/187,552, filed on May 12, 2021.

(51) Int. Cl.
*A61N 1/36* (2006.01)
*H04R 25/00* (2006.01)

(52) U.S. Cl.
CPC ....... *H04R 25/606* (2013.01); *A61N 1/36038* (2017.08); *H04R 25/353* (2013.01);
(Continued)

(58) Field of Classification Search
CPC .... H04R 25/606; H04R 25/353; H04R 25/43; H04R 25/505; H04R 2225/67; A61N 1/36038
See application file for complete search history.

(56) References Cited

U.S. PATENT DOCUMENTS 7,231,257 B2 6/2007 McDermott et al.
7,310,558 B2 12/2007 Van Hoesel
(Continued)

FOREIGN PATENT DOCUMENTS

| | | | |
|---|---|---|---|
| CN | 104307100 | B | 1/2017 |
| EP | 2352550 | B1 | 6/2017 |
| WO | 2021-084400 | A1 | 5/2021 |

OTHER PUBLICATIONS

International Search Report and Written Opinion in counterpart International Application No. PCT/IB2022/053692, mailed Aug. 2, 2022, 8 pages.
(Continued)

*Primary Examiner* — Catherine M Voorhees
(74) *Attorney, Agent, or Firm* — Edell, Shapiro & Finnan, LLC

(57) ABSTRACT

Presented herein are techniques to enhance pitch coding in hearing devices, such as cochlear implants, by utilizing place of stimulation to more accurately and distinctly code frequency information pertaining to individual harmonics of a target harmonic signal, such as voiced vowel in speech or a harmonic tone in music. The techniques presented herein can be combined with a temporal pitch enhancement system to provide a combined system which operates over the voice and musical pitch range in which for example, pitch perception for low fundamental frequencies (F0s) is enhanced via the temporal pitch enhancement method and perception for higher F0s is enhanced via the spectral-place pitch coding method described in the present application. The
(Continued)

techniques presented herein can also have application to enhancing coding of pitch and speech in acoustic hearing devices such as hearing aids.

34 Claims, 23 Drawing Sheets

(52) U.S. Cl.
CPC ........... *H04R 25/43* (2013.01); *H04R 25/505* (2013.01); *H04R 2225/67* (2013.01)

(56) References Cited

U.S. PATENT DOCUMENTS

| | | | | |
|---|---|---|---|---|
| 8,019,431 | B2 | 9/2011 | Nie et al. | |
| 8,260,430 | B2 * | 9/2012 | James ................ | A61N 1/36038 607/57 |
| 8,842,853 | B2 | 9/2014 | Vandali et al. | |
| 9,008,339 | B1 | 4/2015 | Bacon et al. | |
| 9,084,893 | B2 | 7/2015 | Vandali et al. | |
| 9,324,339 | B2 | 4/2016 | Strauss et al. | |
| 9,511,225 | B2 | 12/2016 | Milczynski et al. | |
| 2006/0080087 | A1 * | 4/2006 | Vandali ............. | A61N 1/36038 704/E21.009 |
| 2008/0215332 | A1 * | 9/2008 | Zeng .................. | A61N 1/36038 704/E19.036 |
| 2009/0254150 | A1 | 10/2009 | Zierhofer | |
| 2011/0286618 | A1 * | 11/2011 | Vandali ............. | A61N 1/36038 381/320 |
| 2015/0367132 | A1 * | 12/2015 | Milczynski .......... | A61N 1/0541 607/3 |
| 2021/0360353 | A1 * | 11/2021 | Croghan .............. | H04R 25/356 |

OTHER PUBLICATIONS

Donaldson, G. S., Kreft, H. A., and Litvak, L. (2005). Place-pitch discrimination of single- versus dual-electrode stimuli by cochlear implant users (L). J. Acoust. Soc. Am., 118(2), 623-26, https://doi.org/10.1121/1.1937362.
Vandali, A. E., Whitford, L. A., Plant, K. L., and Clark, G. M. (2000). Speech perception as a function of electrical stimulation rate: Using the Nucleus 24 cochlear implant system. Ear Hear. 21, 608-624, DOI:10.1097/00003446-200012000-00008.
Vandali, A. E., van Hoesel, R. J. M. (2011) Development of a temporal fundamental frequency coding strategy for cochlear implants. J. Acoust. Soc. Am., 129, 4023-36, https://doi.org/10.1121/1.3573988.
Van den Honert, and C., Kelsall, D. C. (2007). Focused intracochlear electric stimulation with phased array channels. J. Acoust. Soc. Am., 121(6), 3703-16, https://doi.org/10.1121/1.2722047.
Wilson, B.S., Finley, C. C., Lawson, D. T., Wolford, R.D., Eddington, D. K., and Rabinowitz, W. M. (1991) Better speech recognition with cochlear implants. Nature 352, 236-238, https://doi.org/10.1038/352236a0.
Speech enhancement for cochlear implant recipients, Dongmei Wang and John H. L. Hansena, https://doi.org/10.1121/1.5031112.

* cited by examiner

PITCH CODING ENHANCEMENT FOR HEARING DEVICES

BACKGROUND

Field of the Invention

The present invention relates generally to hearing devices.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: receiving sound signals at a hearing device; estimating a target fundamental frequency of the received sound signals; determining harmonics of the target fundamental frequency present in the received sound signals; and distinctly coding one or more target harmonics of the target fundamental frequency in stimulation signals delivered to a recipient of the hearing device.

In another aspect, a method is provided. The method comprises: generating a real-time estimate of a time-varying target fundamental frequency of a harmonic signal received at a hearing device; determining information associated with one or more target harmonics of the target fundamental frequency; generating stimulation signals representing the harmonic signal for delivery to a recipient of the hearing device; and increasing, in the stimulation signals, a perceptual distinction between the one or more target harmonics and other components in the harmonic signal.

In another aspect, one or more non-transitory computer readable storage media are provided. The one or more non-transitory computer readable storage media comprise instructions that, when executed by a processor, cause the processor to: estimate a target fundamental frequency of sound signals received at a hearing device; determine information associated with harmonics of the target fundamental frequency; and determine stimulation signals from the sound signals, wherein the stimulation signals are configured to enhance perception of one or more target harmonics of the target fundamental frequency preferential to other signal components.

BRIEF DESCRIPTION OF THE DRAWINGS

Embodiments of the present invention are described herein in conjunction with the accompanying drawings, in which.

DETAILED DESCRIPTION

Figure 1:
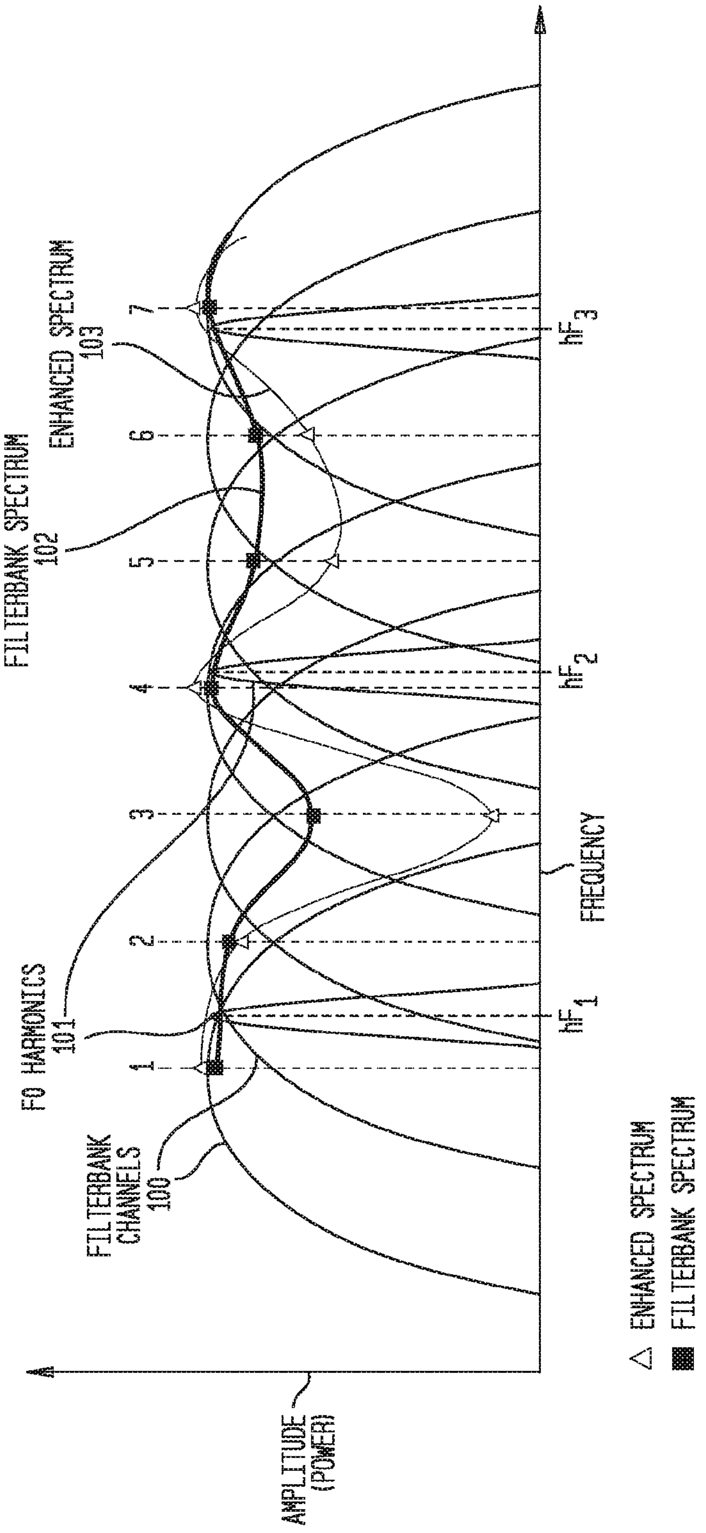
FIG. 1 is a graph illustrating a first method for spectral harmonic enhancement, in accordance with certain embodiments presented herein.

Presented herein are techniques to enhance spectral pitch coding in hearing devices, such as cochlear implants, by utilizing place of stimulation to more accurately and distinctly code frequency information pertaining to individual harmonics of a target harmonic signal, such as voiced vowel in speech or a harmonic tone in music. The techniques presented herein can be combined with a temporal pitch enhancement system to provide a combined system which operates over the voice and musical pitch range in which, for example, pitch perception is enhanced via the temporal pitch enhancement method for low fundamental frequencies (FOs) while perception for higher FOs is enhanced via the spectral-place pitch coding method described in the present application. The techniques presented herein can also have application to enhancing coding of pitch and speech in acoustic hearing devices.

Merely for ease of description, the techniques presented herein are primarily described herein with reference to a specific hearing device system, namely a cochlear implant system. However, it is to be appreciated that the techniques presented herein may also be used with a variety of other implantable medical device systems. For example, the techniques presented herein may be used with other hearing systems, including combinations of any of a cochlear implant, middle ear auditory prosthesis (middle ear implant), bone conduction device, direct acoustic stimulator, electro-acoustic prosthesis, auditory brain stimulator systems, etc. The techniques presented herein may also be used with systems that comprise or include tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Voice-pitch and/or musical-pitch perception by cochlear implant recipients is significantly poorer than that of normal hearing (NH) listeners. This is because fine spectral and temporal structure used by normal hearing listeners to resolve harmonics of the target fundamental frequency (F0) as a cue to pitch cannot be conveyed by conventional cochlear implant systems. Instead weaker temporal envelope cues to F0-pitch are utilized by cochlear implant recipients for low fundamental frequencies (e.g., up to approximately 300 Hz, beyond which discrimination of temporal F0 pitch deteriorates).

In addition, while place of stimulation elicits pitch sensations that can provide a coarse representation of spectral information (e.g., spectral timbre and resonant frequencies), place does not provide a mechanism by which target fundamental frequency (F0) harmonics can be resolved, at least not in the same manner as occurs in normal hearing. This limitation is due, in part, to the broad spatial spread of excitation along the cochlea to electrical stimulation and other differences compared to acoustic stimulation, such as the deterministic manner in which neurons are recruited by electrical stimulation. However, although electrical place is not capable of resolving F0 harmonics in a normal manner, the mechanism may still be capable of providing some discriminating spectral cues to F0, especially for higher FOs (e.g., at or above 300 or 400 Hz depending on the resolution and frequency selectivity of apical filterbank channels) where distinct places of excitation in the cochlea can be produced for individual harmonics of F0.

Further limitations of F0 pitch coding in cochlear implant systems arise because existing clinical sound coding strategies, such as the Advanced Combination Encoder (ACE) strategy and the Continuous Interleaved Sampling (CIS) strategy, poorly extract and code the above-mentioned temporal and spectral cues to F0-pitch. For temporal envelope cues, F0 amplitude modulation coded in the stimulus envelope of channel signals is used to elicit a sensation of pitch. However, the coded depth and shape of this modulation is neither optimal nor consistent. The depth can often be very shallow and variable in level and phase across channels and different signals, and the shape can often contain multiple temporal peaks. Furthermore, the shape and depth of modulation is easily disrupted by noise. As such, coding of temporal F0-pitch cues by existing strategies elicit poor pitch salience and inaccurate pitch-height. In addition, because the F0 modulation is derived from beating between neighboring harmonics passed by each band-pass filterbank channel, the highest F0 modulation frequencies that can be passed are limited by the bandwidth of each channel. Thus, for strategies such as ACE, the temporal envelope cues to pitch coded in apical channels diminish for FOs higher than approximately 200 Hz, further limiting the range of F0 that can be perceived by cochlear implant recipients using temporal coding.

Fortunately, temporal F0-pitch coding can be improved by cochlear implant strategies, albeit for low FOs up to approximately 300 Hz. Furthermore, as discussed earlier, place coding may provide some discriminating cues to F0 harmonic frequencies. However, this is mainly the case for higher FOs (e.g., above 300 or 400 Hz) where sufficient frequency selectivity is provided by the filterbank and stimulating electrodes/neural interface to code individual F0 harmonics at distinctly separate places along the cochlea. In addition, because apical-to-middle band-pass filterbank channels substantially overlap one another, narrow-band signals such as a pure-tone or an F0 partial result in activation of a least three and up to five neighboring channels. Finally, like temporal envelope coding, spectral-place coding of F0 information is disrupted by noise which in this case reduces spectral harmonic contrast, and hence reduces perceptual distinction between harmonic frequencies.

Cochlear Implant Sound Coding System

The techniques presented herein are applicable to, for example, cochlear implant sound coding strategies, such as Continuous Interleaved Sampling (CIS) and Advanced Combination Encoder (ACE) strategy, which employ a filterbank of band-pass filters (BPFs) and temporal envelope detectors to spectrally analyze the sound signal. The techniques presented herein also have application to coding strategies, such as Peak Derived Timing (PDT), and Fine Structure Processing (FSP), which additionally extract and code fine-timing information from the filterbank channels. As described further below, one embodiment for enhancement of spectral harmonic information is shown in FIG. 9 for use in a cochlear implant system 1450, as shown in FIG. 14.

Figure 9:
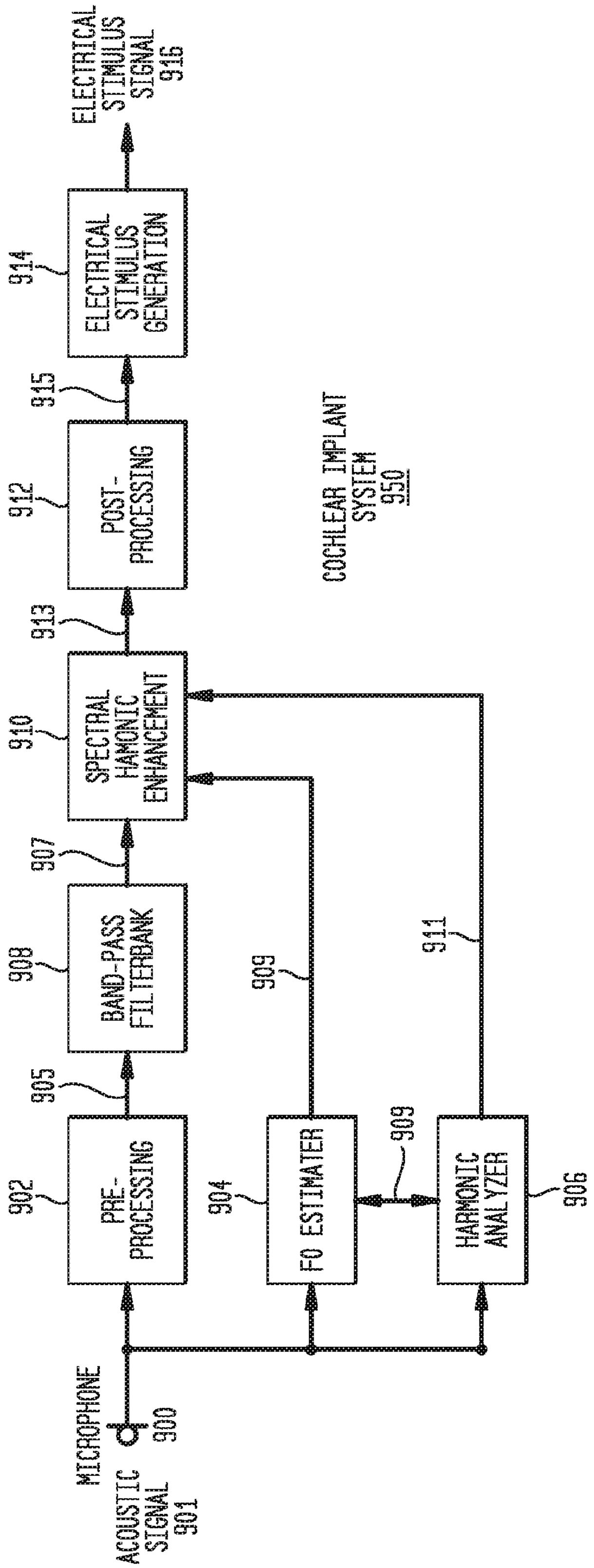
FIG. 9 is a functional block diagram of an example cochlear implant system, in accordance with certain embodiments presented herein.
Figure 14:
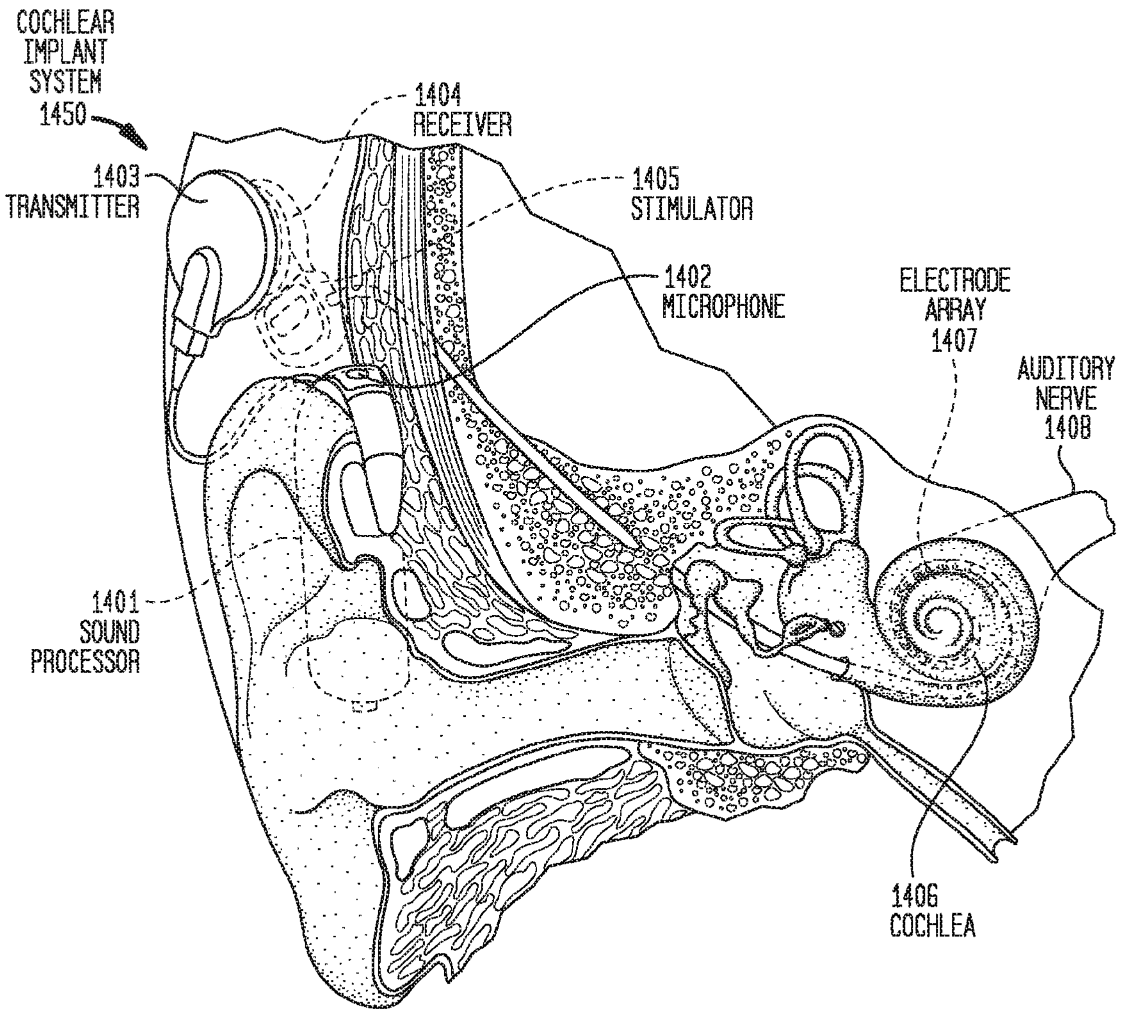
FIG. 14 is a schematic diagram of an example cochlear implant system configured to implement aspects of the techniques presented herein.

More specifically, in the examples of FIGS. 9 and 14, the sound processing and coding is performed by a sound processor 1401 (FIG. 14) which analyzes the sound signals captured/received by an ear-level microphone 1402 (FIG. 14). After some pre-processing of the signal, the filterbank channel output signals (channelized signals) 907 (FIG. 9) are processed and used to produce electrical stimulus signals 916 (FIG. 9), which are transmitted 1403 (FIG. 14) to an implanted receiver-stimulator 1404, 1405 (FIG. 14), which in turn stimulates the auditory nerve 1408 (FIG. 14) via electrical current pulses delivered through an electrode array 1407 within the cochlea 1406. The filterbank channels are mapped tonotopically to the electrode sites within the cochlea and the intensity of the electrical stimulus signals for each channel/electrode are mapped within an individual cochlear implant recipient's perceptual electrical dynamic range. While the present application has specific relevance to electrical stimulation in cochlear implant sound coding systems, it should be appreciated that the proposed processing may also have relevance to acoustic processing such as in hearing aids, wearable acoustic devices, etc.

F0 Estimator and Harmonic Analyzer

In addition to the processing provided by cochlear implant sound coding strategies, the techniques presented herein utilize an F0 estimator 904 (FIG. 9) to estimate the target fundamental frequency (F0) of a target harmonic signal present in the acoustic signal 901 (FIG. 9). The techniques presented herein also utilize a harmonic analyzer 906 (FIG. 9) to analyze the harmonic structure (i.e., harmonic frequencies and powers) of the target harmonic signal and/or the frequencies and powers of any inharmonic or non-target harmonic signals present in the captured/measured acoustic signal 901 (FIG. 9).

The role of the F0 estimator is to provide a real-time estimate (i.e., with as little time-lag as possible) of the near-instantaneous (time-varying) F0 pertaining to some target harmonic signal. The target harmonic signal is typically produced by an acoustic source located in front of the recipient (listening device) and/or is the most dominant sound source in the recipient's range of hearing. The target harmonic signal could, for example, correspond to voiced speech (e.g., a vowel) produced by a talker or to a harmonic tone produced by a musical instrument. The F0 estimator is also used to provide an estimate of how much of the energy in the incoming signal is related to the target harmonic signal at any point in time. The target harmonic signal power-to-noise power ratio, or the target harmonic signal power-to-total power ratio, are useful measures in that regard.

The role of the harmonic analyzer is to provide information about the frequency components (partials) present in the incoming sound/signal at any point in time. Specifically, for cases when a target harmonic signal is present in the incoming signal for which the F0 estimator has provided an estimate of the target F0, the harmonic analyzer in turn provides a measure of the frequency and power of any harmonics of the target F0 in the incoming signal. The harmonic analyzer also provides a measure of the frequency and power (or intensity) of inharmonic partials produced by any inharmonic signals in the incoming signal, or the frequency and power of non-target signal components when no target harmonic signal is detected. A variety of techniques can be used to generate the real-time F0 and harmonic information estimates.

Spectral F0 Enhancement—Enhanced Place Coding of Harmonic Frequencies

The techniques presented herein are also configured to enhance the spectral harmonic coding of a target harmonic signal. Several methods for enhancing frequency-place coding of target F0 harmonics are presented below. It should be appreciated that a variety of different rules/functions can be used to adjust the channel gains/stimulation levels with the aim of increasing target F0 harmonic distinction/contrast and accuracy in the filterbank channels and hence in subsequent coding of harmonic place-pitch information.

Harmonic Spectrum Enhancement (Method 1)

FIG. 1 is a frequency domain graph illustrating the frequency (abscissa) relative to the amplitude/power (ordinate) of an incoming/received sound signal (incoming signal). In FIG. 1, for each harmonic 101 (e.g., $hF_1$, $hF_2$, $hF_3$) of a target F0 harmonic signal, the relative contribution of each filterbank channel (lines 100 in FIG. 1) to that harmonic (points/line 102) in FIG. 1 can be adjusted to enhance the spectral contrast (and hence perceptual distinction) between harmonics and generate the enhanced harmonic spectrum (points/line 103) in FIG. 1. That is, line 102 of FIG. 1 generally represents the standard (non-enhanced) channelized outputs/spectrum of a hearing device filterbank. In contrast, line 103 represents the enhance spectrum generated in accordance with certain embodiments presented herein. As shown, and as described further below, the techniques presented shown in FIG. 1 enhance (increase) the spectral contrast of harmonic information in the spectrum (e.g., specifically targeted for enhancement of the harmonics).

In these techniques, the gain for channels that carry most of each harmonic's energy can be adjusted to pass (or even amplify) the harmonic energy, while the gain for channels that carry less, or no harmonic energy can be adjusted to attenuate (or block) the channel signals. This rule would act to increase spectral harmonic contrast of the target F0 harmonic signal, particularly in apical (low frequency) channels where the spacing between channels is sufficiently fine enough to separate individual harmonics.

When the gain of channels away from the harmonic frequency (i.e., that carry less of the harmonic power) are reduced, the overall loudness of the coded harmonic signal is also reduced. To compensate for this, gain is applied to channels closest to the harmonic frequency (i.e., to those channel that carry most of the harmonic power) so as to preserve the overall harmonic power measured from all filterbank channels responsive to the harmonic frequency. For instance, for the first harmonic ($hF_1$) in FIG. 1, the harmonic power measured in filterbank channels 1, 2, and 3 (see first 3 points associated with line 102 in FIG. 1) are summed and used to determine the overall gain applied to the adjusted (enhanced) channel gains so that the adjusted channel power (see first 3 points associated with line 103 in FIG. 1) remains equal to the measured harmonic power. Furthermore, for cases when noise power (i.e., inharmonic or non-target signal) is also passed by a channel, the channel gain is adjusted to account for (or remove) the contribution of that within-channel noise. This is done by establishing the target channel power from the measured harmonic channel power which is used to determine the gain applied to the total (harmonic+noise) channel power.

For cases when there is no target F0 harmonic signal (i.e., when the target signal is inharmonic or absent), channel gain processing is adapted so that coding of non-target and inharmonic spectral information is not enhanced. This rule in general adapts the amount of spectral enhancement applied (i.e., the degree to which filterbank channel gains are adjusted) proportionally to the target harmonic signal-to-noise ratio (or target harmonic signal-to-total signal ratio).

Harmonic Coding in Two Adjacent Channels (Method 2)

In another embodiment presented herein, a similar rule to that described above with reference to FIG. 1 can be used to ensure that only two adjacent channels (see points/lines 203 in FIG. 2) are activated to code frequency (via place of stimulation) and power, or intensity, (via level of stimulation) of individual target F0 harmonics, as opposed to all of the channels that contain some energy related to each harmonic. It is noted that filterbanks in existing cochlear implant strategies have considerably channel overlap which generally produce stimulation on three and up to five adjacent apical channels when coding narrow-band signals such as individual harmonics. This overlap serves to "smear" the harmonic information in the channelized signals. In a fully sequential coding strategy (without current steering), the stimulus amplitudes for two sequentially stimulated adjacent channels can be controlled (e.g., using the spectral centroid for the two channels) so that the mean place and intensity of activation for the electrode pair elicits a percept that corresponds to (or is mapped according to) the target frequency and power, which may fall intermediately between the pair of channels/electrodes.

Figure 2:
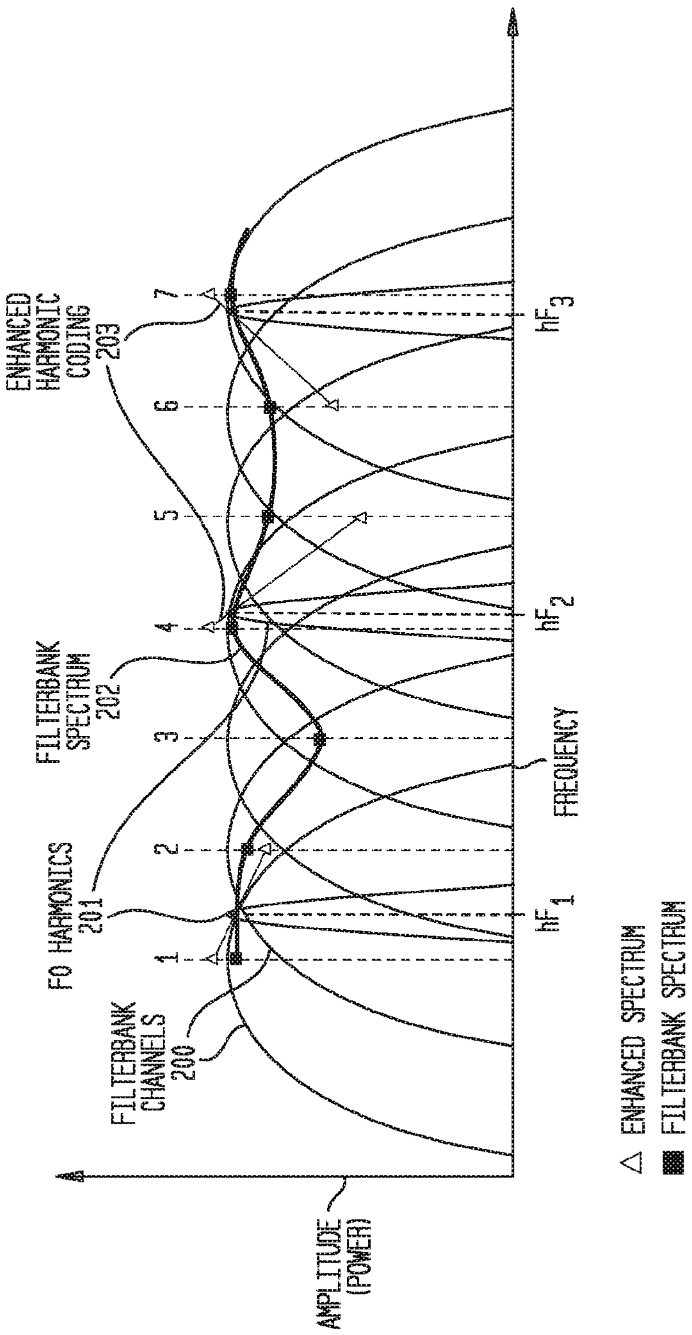
FIG. 2 is a graph illustrating a second method for spectral harmonic enhancement, in accordance with certain embodiments presented herein.

For instance, FIG. 2 is a frequency domain graph illustrating the frequency (abscissa) relative to the amplitude/power (ordinate) of an incoming/received sound signal (incoming signal). In FIG. 2, it can be seen that the power-weighted mean frequency-place of stimulation (spectral centroid) for each pair of adjacent channels (see points associated with 203 in FIG. 2) code the frequency and power (intensity) of each target harmonic 201 (e.g., $hF_1$, $hF_2$, $hF_3$) in FIG. 2. Similar to line 102 of FIG. 1, line 202 of FIG. 2 generally represents the standard (non-enhanced) channelized outputs/spectrum of a hearing device filterbank. Note, as was the case for method 1, the overall channel gains or stimulation level (e.g., level/intensity of stimulation) needed to code each target harmonic are adjusted to preserve the measured harmonic power while accounting for any within-channel noise power. In addition, for cases when there is no target FO harmonic signal, channel gain processing is adapted so that coding of non-target and inharmonic spectral information is not enhanced.

Figure 4A:
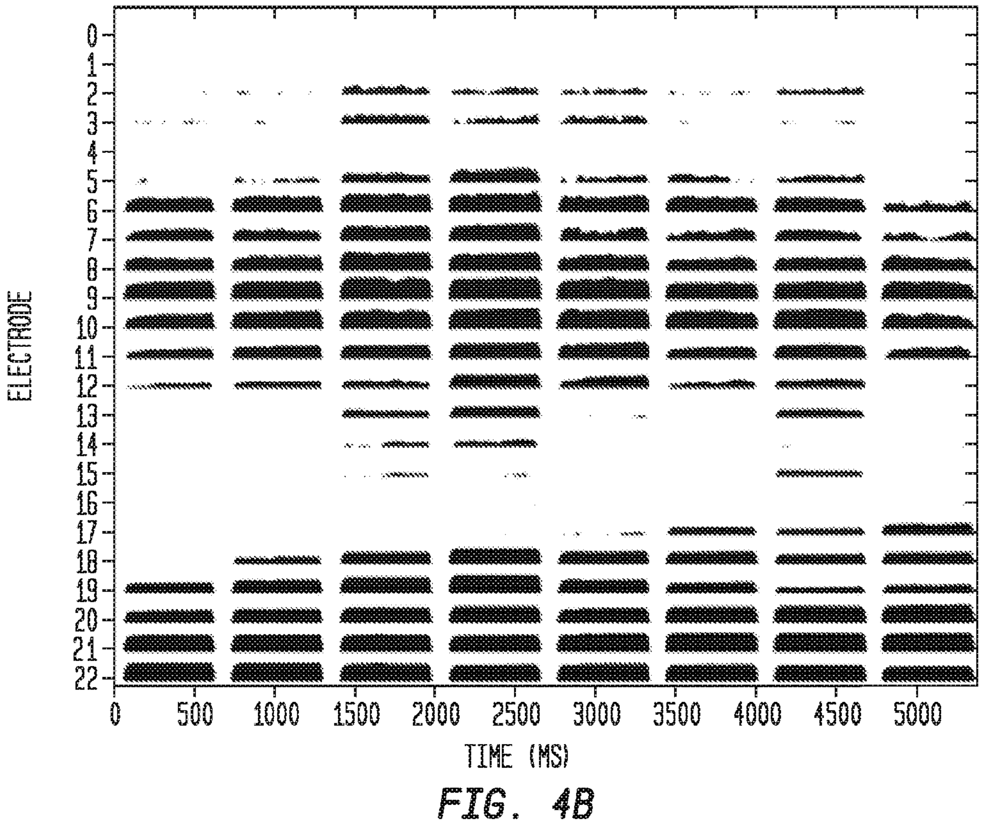
FIG. 4A illustrates a non-enhanced electrical stimulation pattern generated using the Continuous Interleaved Sampling (CIS) strategy for vowel /e/ sung by a female singer at FOs ranging from C4 (262 Hz) to G4 (392 Hz) increasing in one semitone steps.
Figure 4B:
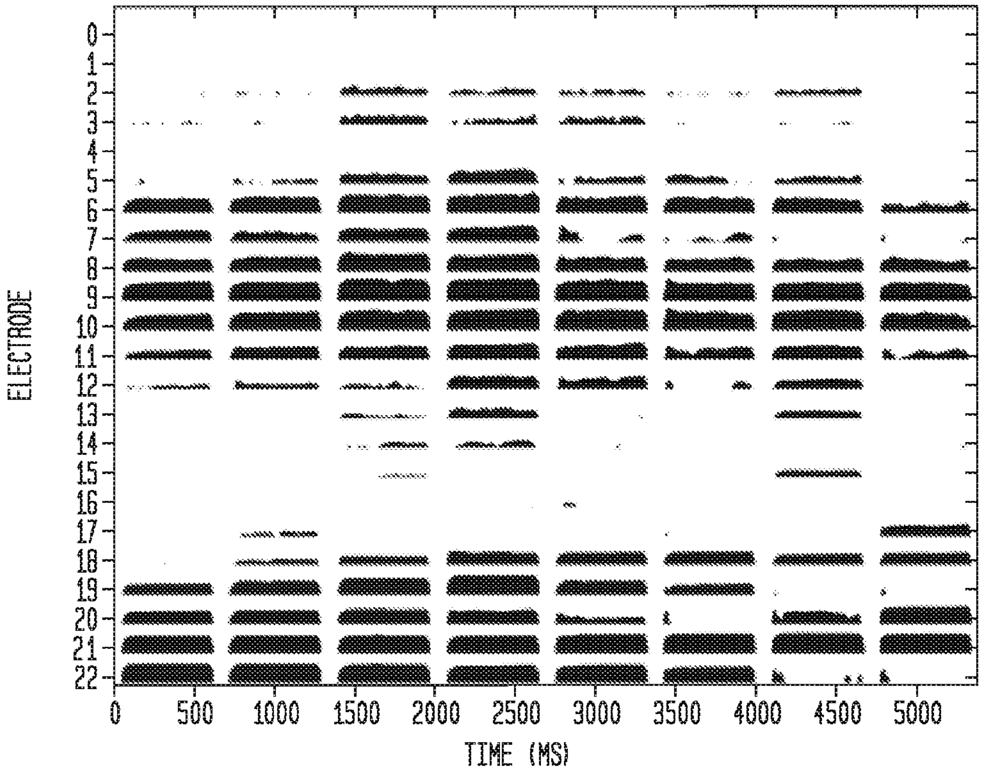
FIG. 4B illustrates an electrical stimulation pattern generated using the CIS strategy for vowel /e/ sung by a female singer at FOs ranging from C4 (262 Hz) to G4 (392 Hz) increasing in one semitone steps, where the electrical stimulation pattern is enhanced using the second spectral harmonic enhancement presented herein.

Examples of non-enhanced and enhanced electrical stimulus patterns (using method 2) are shown in FIGS. 4A-4D for a sung vowel /e/, produced at increasing FOs from C4 (262 Hz) to G4 (392 Hz), by a female singer. More specifically, FIGS. 4A and 4B illustrate electrical stimulation patterns for a CIS strategy for vowel /e/ sung by a female singer at FOs ranging from C4 (262 Hz) to G4 (392 Hz) increasing in one semitone steps. FIG. 4A illustrates non-enhanced/standard electrical stimulation patterns, while FIG. 4B illustrates spectral harmonic enhancement (method 2). For each electrical stimulation pattern (electrodogram), each stimulation pulse is plotted as a black vertical line with line-height reflecting the stimulus current-level at a position corresponding to the activated electrode and time of stimulation. Electrode number is plotted on the ordinate and time (in milliseconds) on the abscissa. Electrode number 22 is the most apical (lowest frequency) and 1 the most basal (highest frequency) electrode.

Figure 4C:
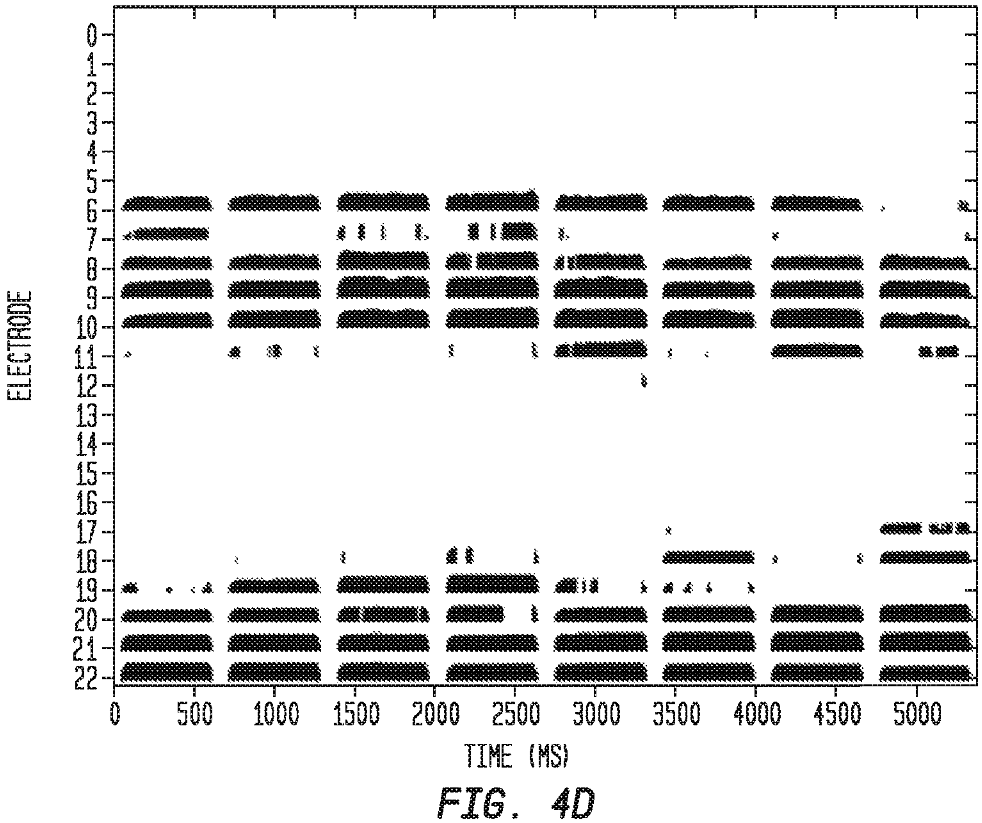
FIG. 4C illustrates a non-enhanced electrical stimulation pattern generated using the Advanced Combination Encoder (ACE) strategy for vowel /e/ sung by a female singer at FOs ranging from C4 (262 Hz) to G4 (392 Hz) increasing in one semitone steps.
Figure 4D:
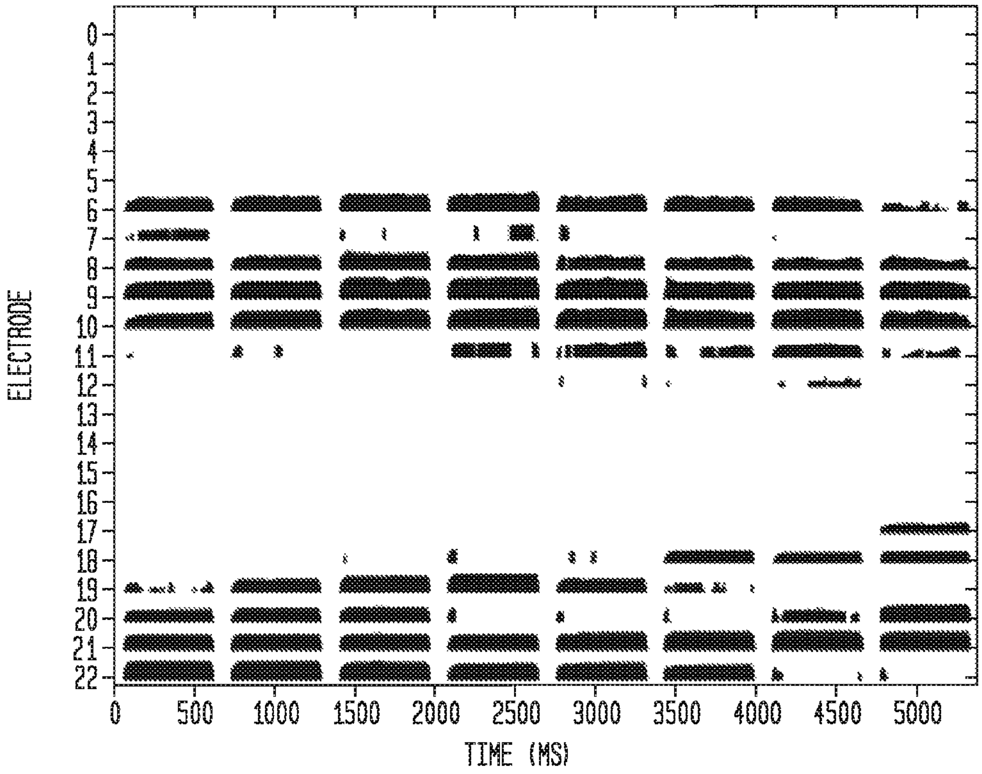
FIG. 4D illustrates an electrical stimulation pattern generated using the ACE strategy for vowel /e/ sung by a female singer at FOs ranging from C4 (262 Hz) to G4 (392 Hz) increasing in one semitone steps, where the electrical stimulation pattern is enhanced using the second spectral harmonic enhancement presented herein.

FIGS. 4C and 4D illustrate electrical stimulation patterns for the ACE strategy (e.g., with selection of 8 largest spectral maxima) for vowel /e/ sung by a female singer at FOs ranging from C4 (262 Hz) to G4 (392 Hz) increasing in one semitone steps. FIG. 4C illustrates non-enhanced/standard electrical stimulation patterns, while FIG. 4D illustrates spectral harmonic enhancement (method 2)

For F0s of approximately 300 Hz and higher (e.g., from the fourth or fifth sung note/stimulus onward in FIGS. 4B and 4D), greater harmonic contrast is visible for the spectral enhancement processing where the place of low-order harmonics is coded by only a pair of adjacent channels/electrodes.

Figure 5A:
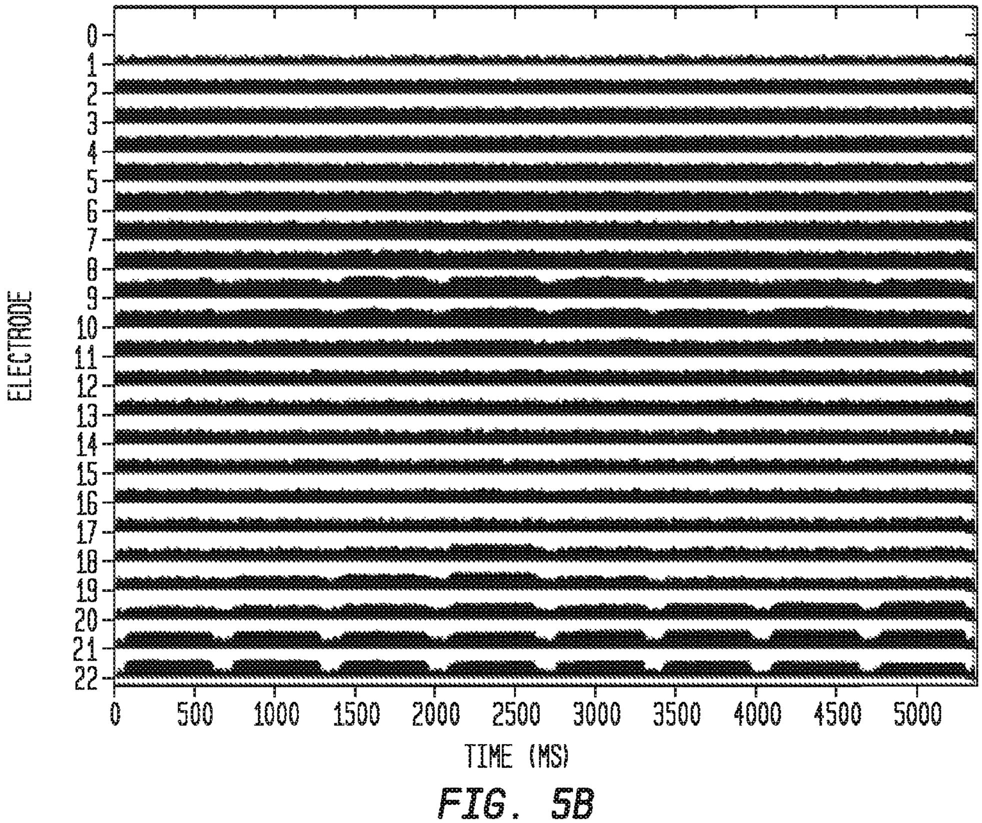
FIG. 5A illustrates a non-enhanced electrical stimulation pattern generated using the CIS strategy for vowel /e/ sung by a female singer at FOs ranging from C4 (262 Hz) to G4 (392 Hz) increasing in one semitone steps with the addition of white noise at a SNR of +4 dB.
Figure 5B:
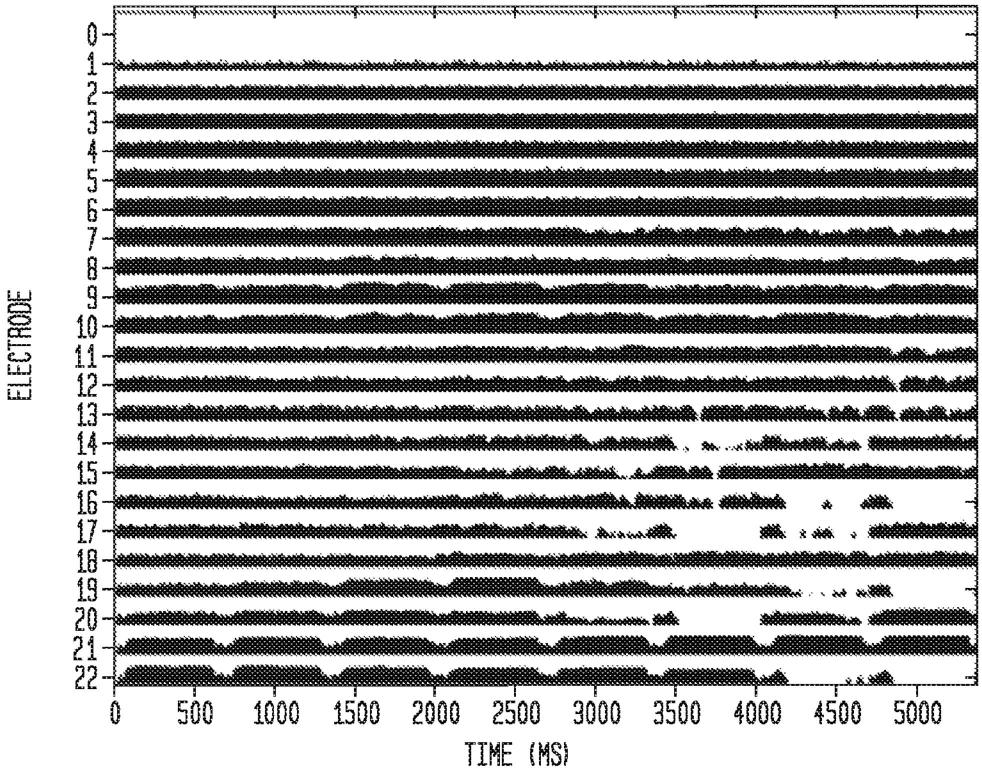
FIG. 5B illustrates an electrical stimulation pattern generated using the CIS strategy for vowel /e/ sung by a female singer at FOs ranging from C4 (262 Hz) to G4 (392 Hz) increasing in one semitone steps with the addition of white noise at a SNR of +4 dB, where the electrical stimulation pattern is enhanced using the second spectral harmonic enhancement presented herein.
Figure 5C:
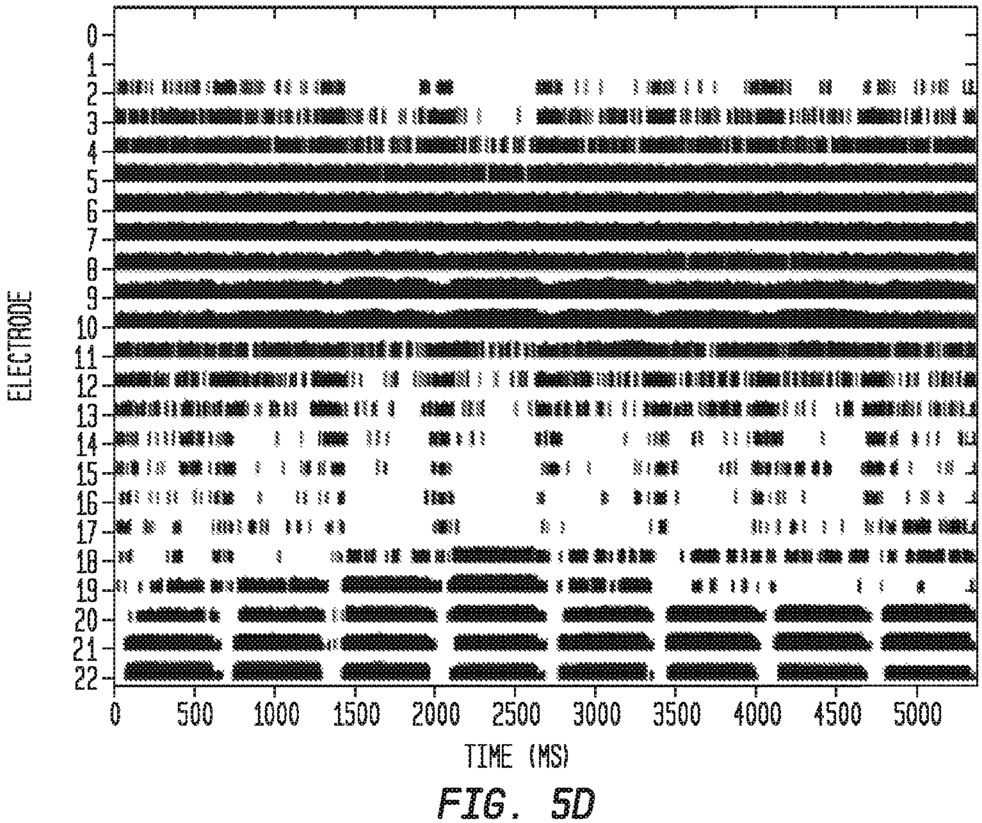
FIG. 5C illustrates a non-enhanced electrical stimulation pattern generated using the ACE strategy for vowel /e/ sung by a female singer at FOs ranging from C4 (262 Hz) to G4 (392 Hz) increasing in one semitone steps with the addition of white noise at a SNR of +4 dB.
Figure 5D:
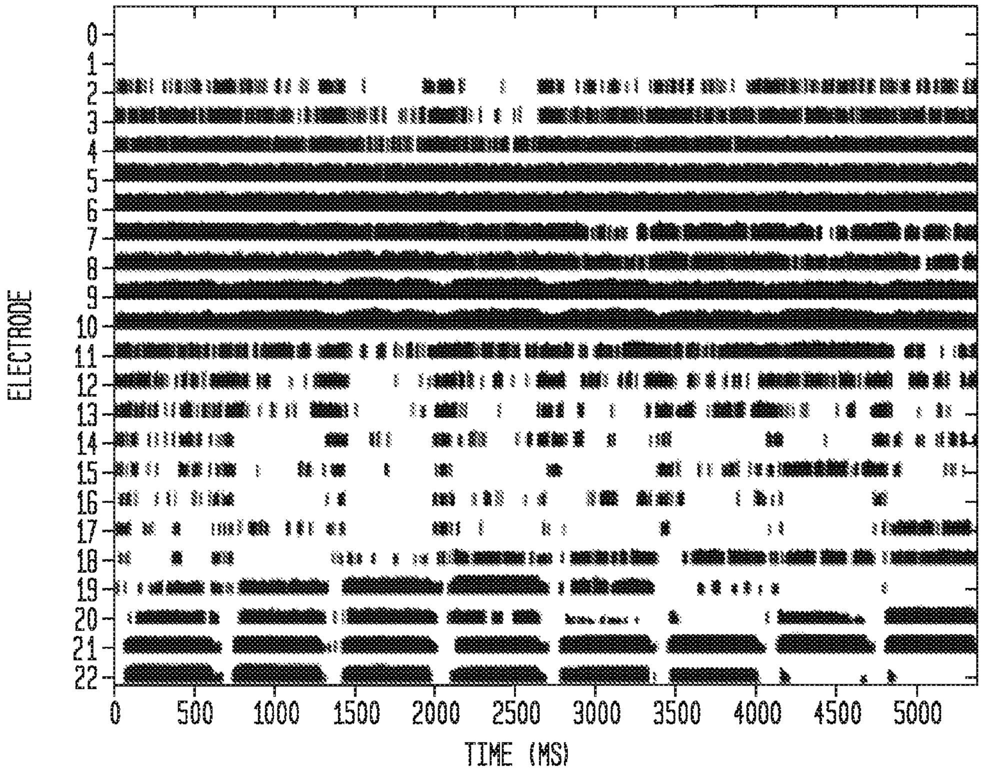
FIG. 5D illustrates an electrical stimulation pattern generated using the ACE strategy for vowel /e/ sung by a female singer at FOs ranging from C4 (262 Hz) to G4 (392 Hz) increasing in one semitone steps with the addition of white noise at a SNR of +4 dB, where the electrical stimulation pattern is enhanced using the second spectral harmonic enhancement presented herein.

FIGS. 5A-5D show the stimulus output patterns for the same signal shown in FIGS. 4A-4D, but with the addition of white noise at a SNR of +4 dB demonstrating the robustness of the technique to noise. That is, FIGS. 5A and 5B illustrate electrical stimulation patterns for the CIS strategy for vowel /e/ sung by a female singer at F0s ranging from C4 (262 Hz) to G4 (392 Hz) in one semitone steps in white noise at an SNR of +4 dB. FIG. 5A illustrates non-enhanced/standard electrical stimulation patterns, while FIG. 5B illustrates spectral harmonic enhancement (method 2). FIGS. 5C and 5D illustrate electrical stimulation patterns for the ACE strategy for vowel /e/ sung by a female singer at F0s ranging from C4 (262 Hz) to G4 (392 Hz) in one semitone steps in white noise at an SNR of +4 dB. FIG. 5C illustrates non-enhanced/standard electrical stimulation patterns, while FIG. 5D illustrates spectral harmonic enhancement (method 2).

There is, however, a constraint on the lowest F0 that can be coded via this method 2 which is imposed by the number of filterbank channels and the number of corresponding electrode sites. Because two adjacent channels are used to code intermediate electrode place pitch, the lowest F0 harmonic spacing that can be resolved is limited by the frequency spacing between pairs of adjacent channels, which in this example is around 250 Hz for apical filterbank channels given a channel spacing of 125 Hz (an F0 of 250 Hz being double the channel spacing of 125 Hz). In contrast, for an F0 of three times the channel spacing (e.g., 375 Hz) or higher, pairs of channels can be used to code each harmonic with no stimulation produced in the intervening channel(s) between harmonic channel pairs, thereby potentially eliciting greater spectral distinction between coded harmonics. For the example shown in FIG. 2, F0 is approximately 2.7 times the apical channel spacing and so while harmonics can be coded using a pair of adjacent channels, only the first two harmonics ($hF_1$, $hF_2$) are separated by an intervening channel which is not activated (in this example channel #3). In order to smoothly deal with this constraint for different F0s and channel spacings, the spectral enhancement approach is progressively reduced/gated-off with decreasing F0s using rules described later as a secondary feature of the present invention. According to those rules, for method 2 and the examples shown in FIGS. 4A-4D and 5A-5D, the F0 transition range is defined so that the applied spectral enhancement is maximal for F0s of approximately 350 Hz (SFOHT) and higher, but minimal (i.e. no enhancement) for F0s of 250 Hz (SFOLT) and lower.

Harmonic Coding Quantized to a Single Channel (Method 3)

Figure 3:
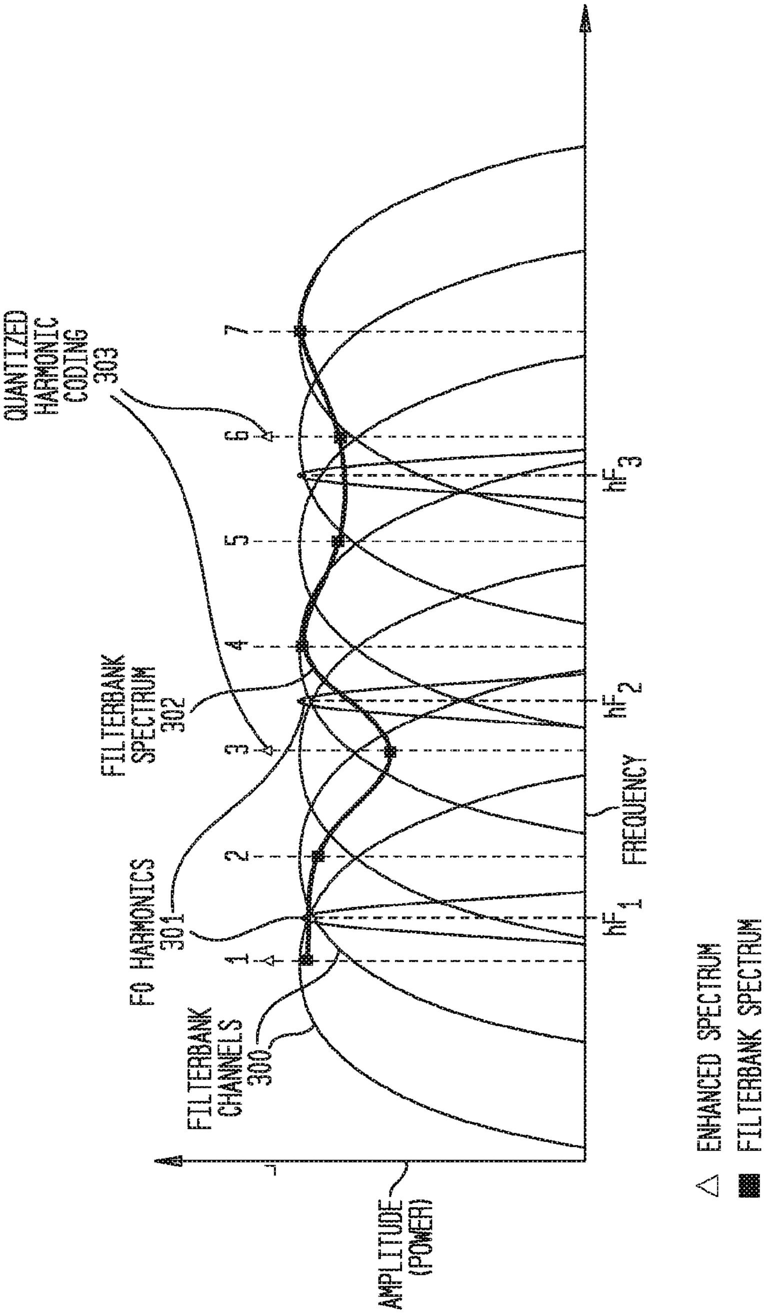
FIG. 3 is a graph illustrating a third method for spectral harmonic enhancement, in accordance with certain embodiments presented herein.

For F0s within the F0 transition range described in method 2 in which the applied spectral enhancement is progressively reduced for lower F0s, it is still possible to provide greater spectral distinction between harmonics at the expense of poorer accuracy in harmonic place coding. In this case, the frequency and power (intensity) of each harmonic 301 is coded using a single channel/electrode site which is closest in place to the harmonic frequency, i.e., the harmonic frequency is quantized to the nearest single electrode site (points 303 in figure). Similar to line 102 of FIG. 1, line 302 of FIG. 3 genreally represents the standard (non-enhanced) channelized outputs/spectrum of a hearing device filterbank. Note, as was the case for method 1, the gain applied to each channel 300 (or stimulation level/intensity of stimulation) used to code a target harmonic must be adjusted to preserve the measured harmonic power while accounting for any within-channel noise power. In addition, for cases when there is no target F0 harmonic signal, channel gain processing is adapted so that coding of non-target and inharmonic spectral information is not enhanced.

Figure 6A:
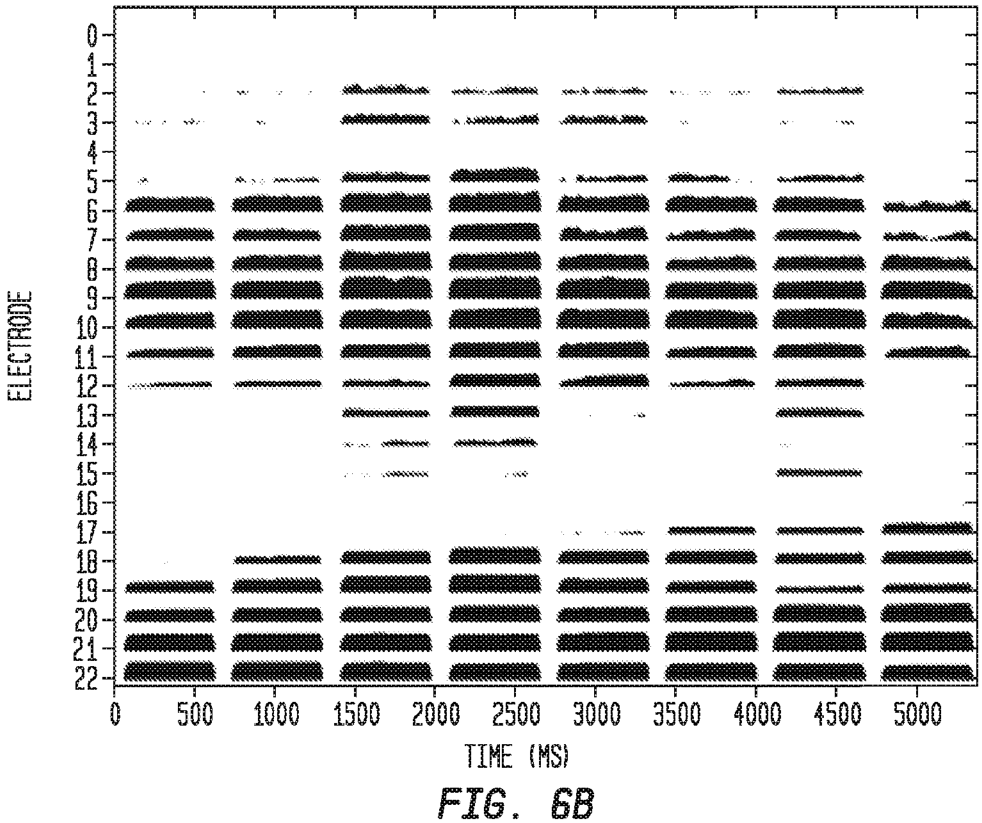
FIG. 6A illustrates a non-enhanced electrical stimulation pattern generated using the CIS strategy for vowel /e/ sung by a female singer at FOs ranging from C4 (262 Hz) to G4 (392 Hz) increasing in one semitone steps.
Figure 6B:
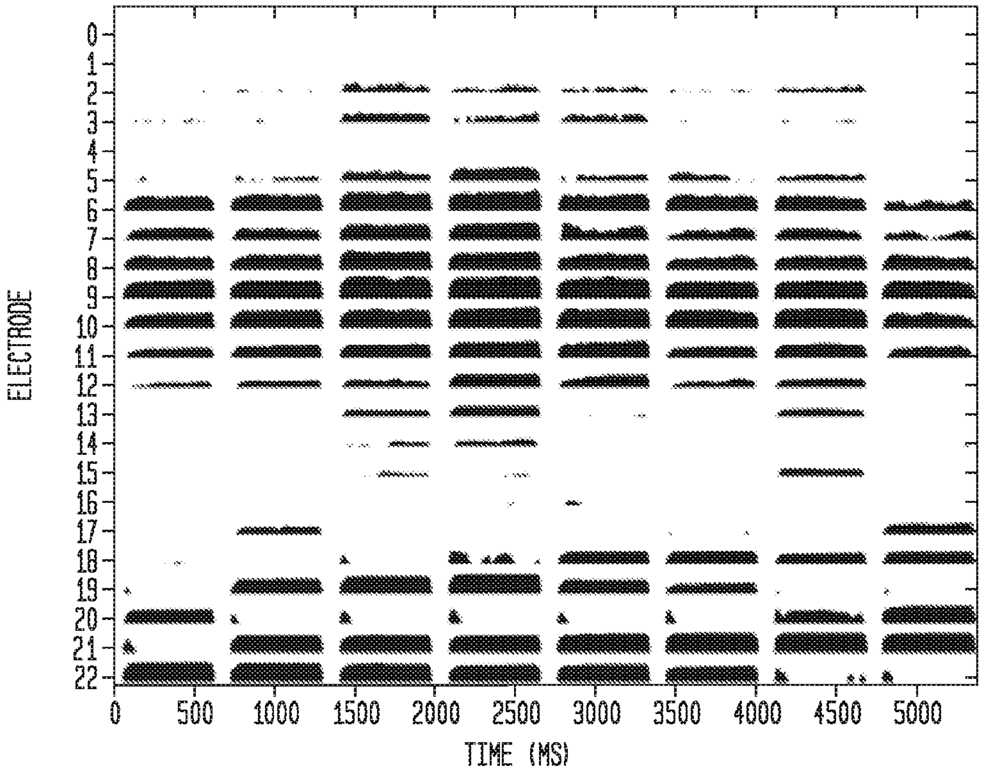
FIG. 6B illustrates an electrical stimulation pattern generated using the CIS strategy for vowel /e/ sung by a female singer at FOs ranging from C4 (262 Hz) to G4 (392 Hz) increasing in one semitone steps, where the electrical stimulation pattern is enhanced using the third spectral harmonic enhancement presented herein.
Figure 6C:
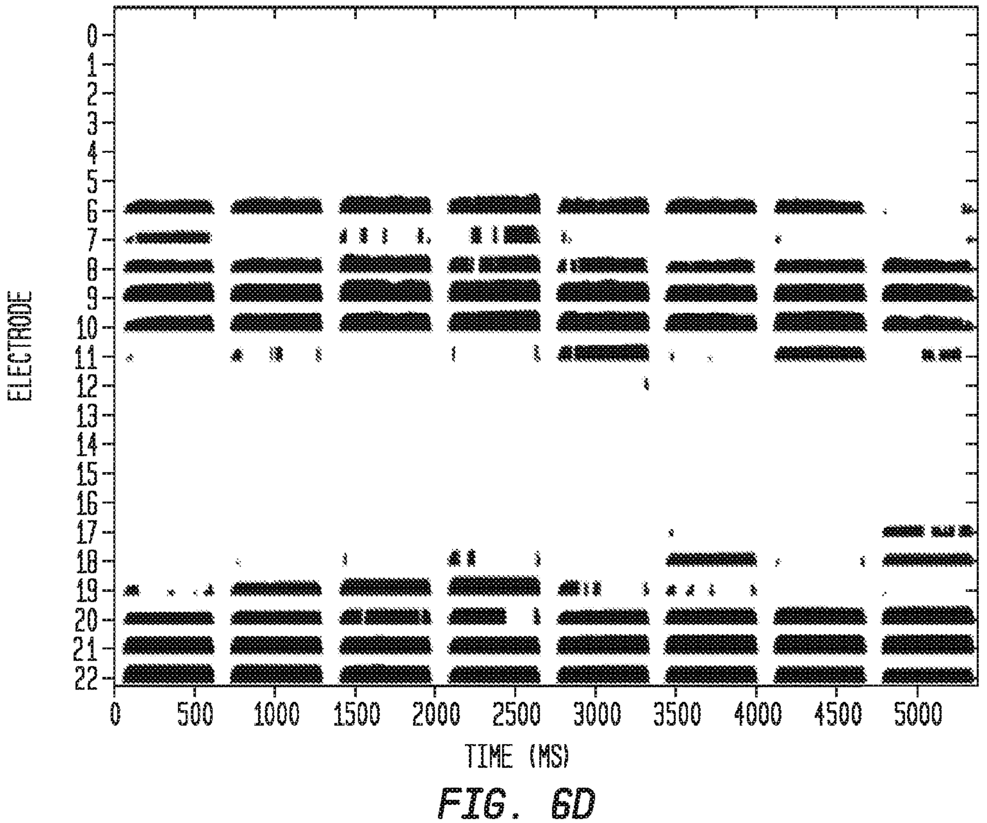
FIG. 6C illustrates a non-enhanced electrical stimulation pattern generated using the ACE strategy for vowel /e/ sung by a female singer at FOs ranging from C4 (262 Hz) to G4 (392 Hz) increasing in one semitone steps.
Figure 6D:
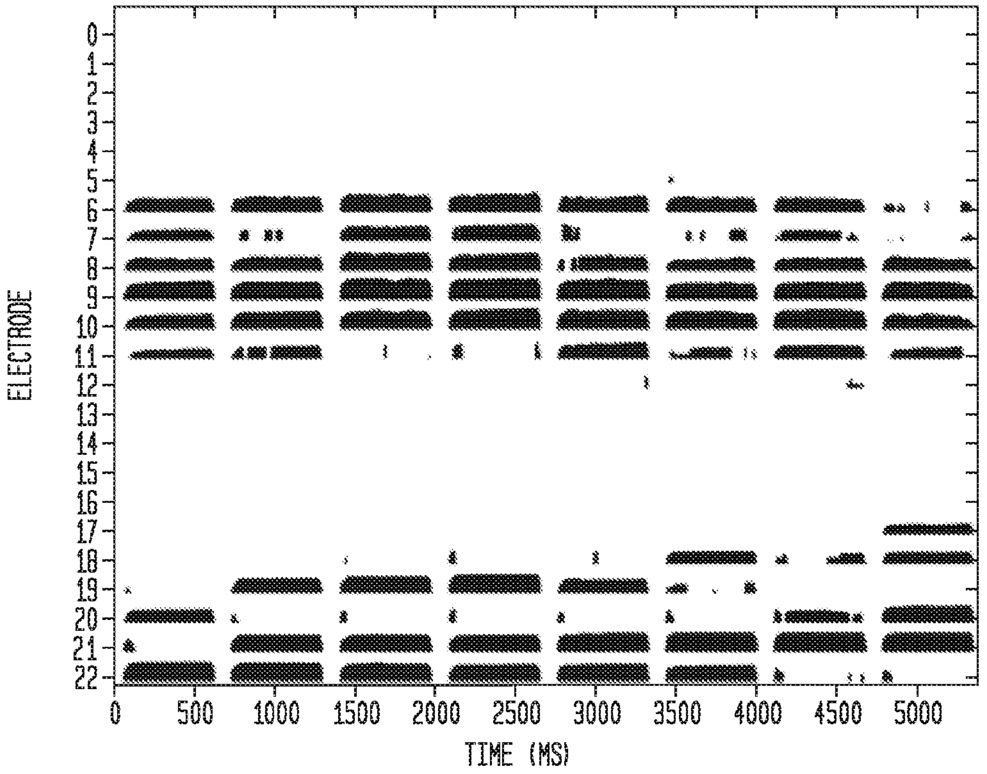
FIG. 6D illustrates an electrical stimulation pattern generated using the ACE strategy for vowel /e/ sung by a female singer at FOs ranging from C4 (262 Hz) to G4 (392 Hz) increasing in one semitone steps, where the electrical stimulation pattern is enhanced using the third spectral harmonic enhancement presented herein.

Example stimulus output patterns for the same signal shown in FIGS. 4A-4D are shown in FIGS. 6A-6D, but using a single channel to code F0 harmonic frequency/place information (method 3) for cases when there is insufficient frequency resolution (channel spacing) to distinctly code an individual harmonic using a pair of adjacent channels as per method 2. In particular, FIGS. 6A and 6B illustrate electrical stimulation patterns for CIS strategy for vowel /e/ sung by a female singer at F0s ranging from C4 (262 Hz) to G4 (392 Hz) in one semitone steps, where FIG. 6A illustrates the non-enhanced spectrum and FIG. 6B illustrates the spectral harmonic enhancement (method 3). FIGS. 6C and 6D illustrate electrical stimulation patterns for the ACE strategy (i.e., with selection of 8 largest spectral maxima) for vowel /e/ sung by a female singer at F0s ranging from C4 (262 Hz) to G4 (392 Hz) in one semitone steps, where FIG. 6C illustrates the non-enhanced spectrum and FIG. 6D illustrates the spectral harmonic enhancement (method 3). It is noted that, when there is sufficient channel spacing to code a harmonic using two channels, method 2 can be applied.

Stimulus output patterns which compare method 2 to 3 are shown in FIGS. 7A-7C and 8A-8C for a harmonic tone in which F0 is swept from 75 to 400 Hz and for the vowel /a/ sung by a female at F0s ranging from C4 (262 Hz) to G4 (392 Hz), respectively. In these examples and those shown in FIGS. 6B and 6D the F0 transition range for method 3 is adjusted so that F0s above 175 Hz ($SF0_{HT}$) are fully enhanced while no enhancement is applied for F0s below 125 Hz ($SF0_{LT}$).

Figure 7A:
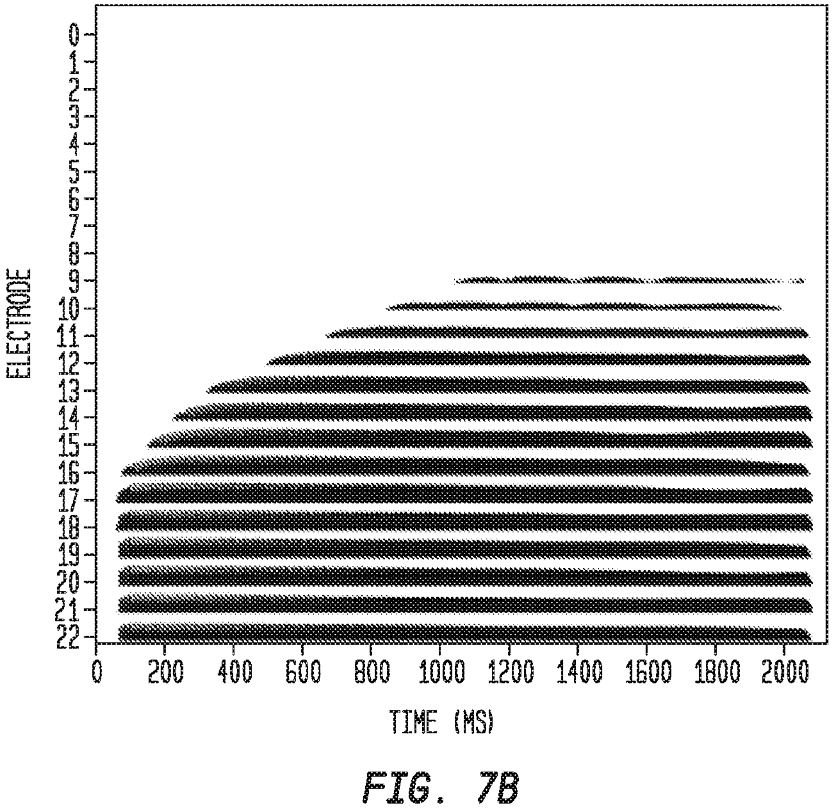
FIG. 7A illustrates a non-enhanced electrical stimulation pattern generated using the CIS strategy for a low pass filtered harmonic tone with F0 swept from 75 to 400 Hz.
Figure 7B:
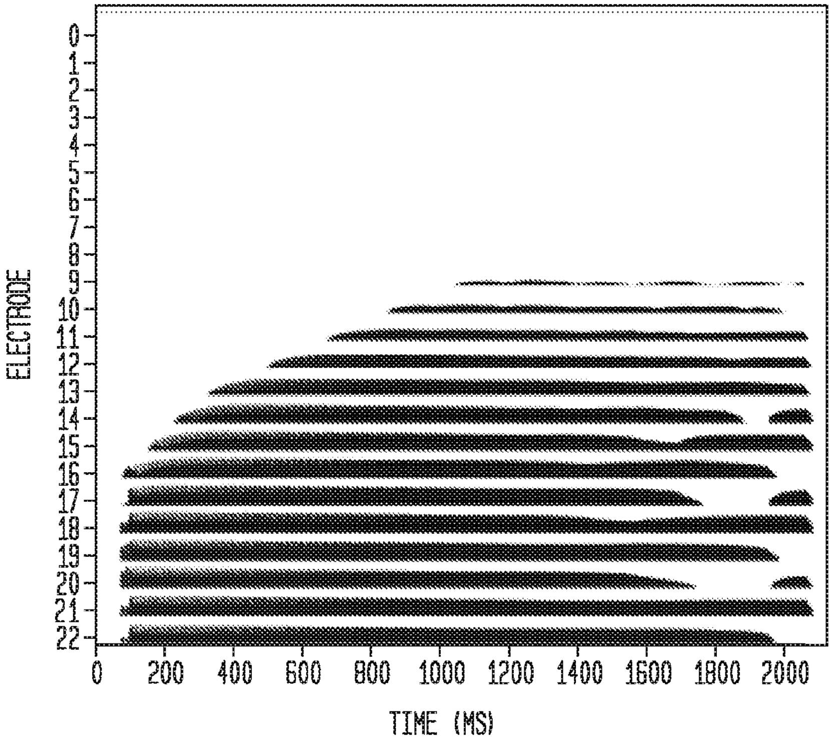
FIG. 7B illustrates an electrical stimulation pattern generated using the CIS strategy for a low pass filtered harmonic tone with F0 swept from 75 to 400 Hz with spectral enhancement in accordance with the second spectral enhancement method.
Figure 7C:
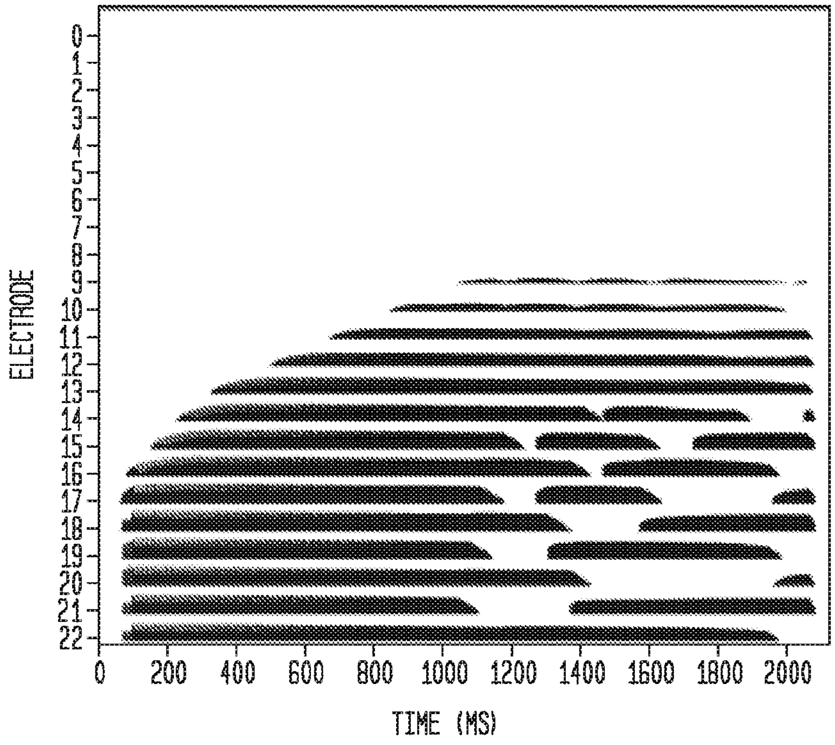
FIG. 7C illustrates an electrical stimulation pattern generated using the CIS strategy for a low pass filtered harmonic tone with F0 swept from 75 to 400 Hz with spectral enhancement in accordance with the third spectral enhancement method.
Figure 8A:
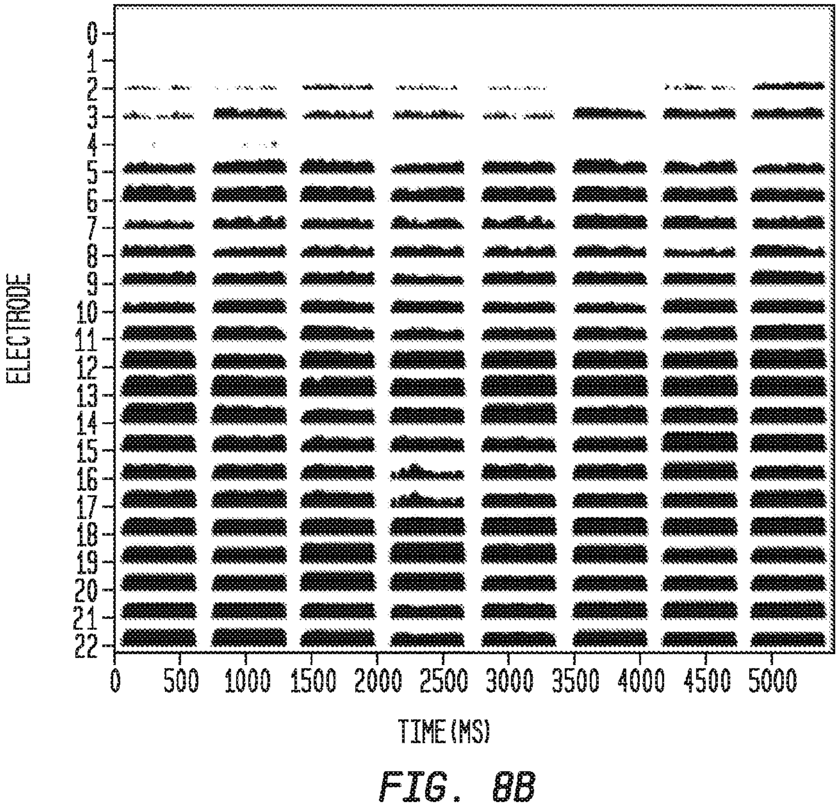
FIG. 8A illustrates a non-enhanced electrical stimulation pattern generated using the CIS strategy for vowel /a/ sung by a female singer at FOs ranging from C4 (262 Hz) to G4 (392 Hz)
Figure 8B:
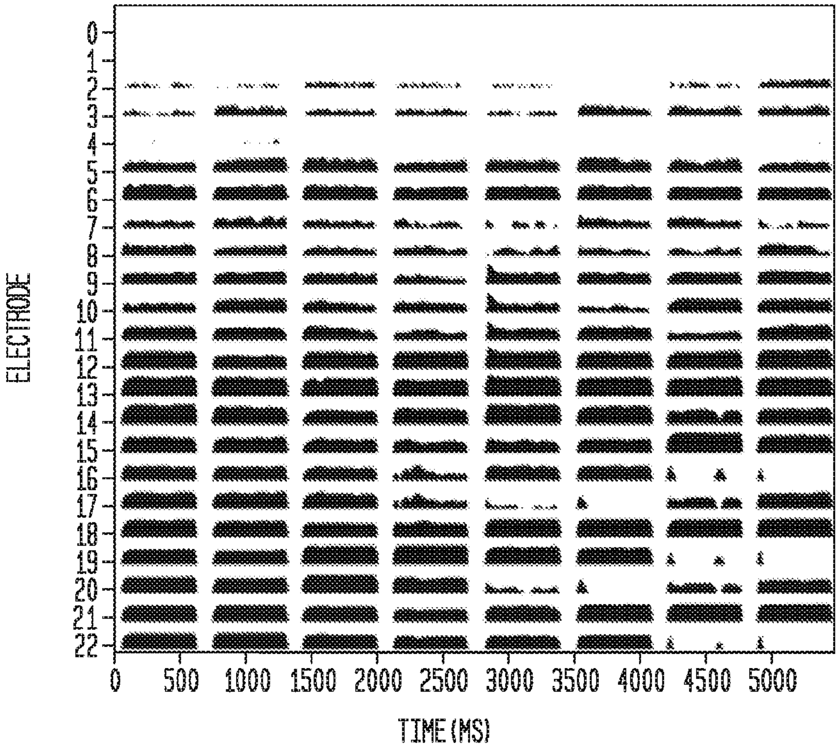
FIG. 8B illustrates an electrical stimulation pattern generated using the CIS strategy for vowel /a/ sung by a female singer at FOs ranging from C4 (262 Hz) to G4 (392 Hz) accordance with the second spectral enhancement method.
Figure 8C:
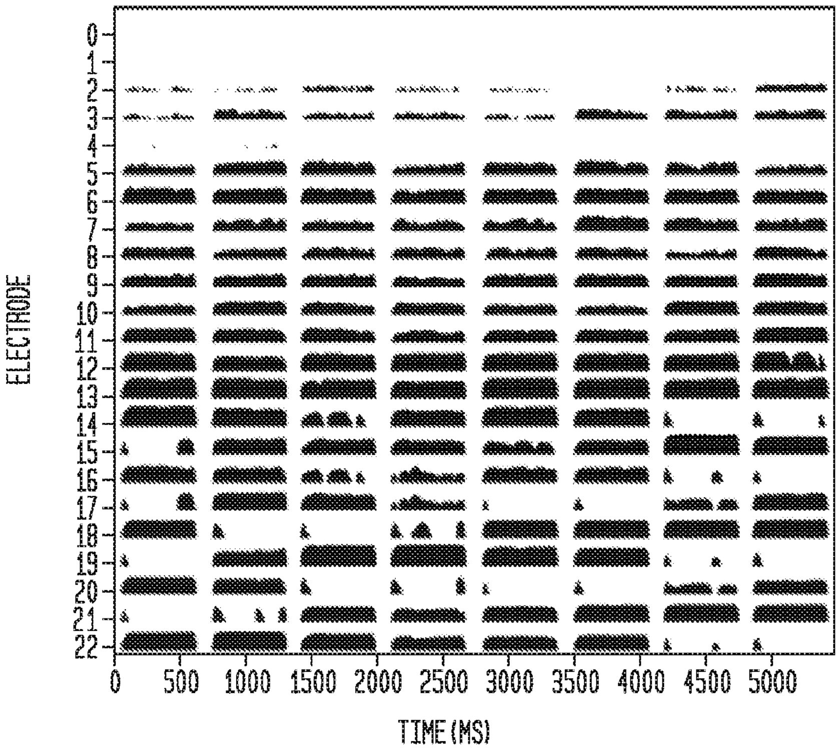
FIG. 8C illustrates an electrical stimulation pattern generated using the CIS strategy for vowel /a/ sung by a female singer at FOs ranging from C4 (262 Hz) to G4 (392 Hz) accordance with the third spectral enhancement method.

In particular, FIGS. 7A-7C illustrate electrical stimulation patterns for the CIS strategy for a low pass filtered harmonic tone with F0 swept from 75 to 400 Hz. FIG. 7A illustrates no enhancement, FIG. 7B illustrates spectral enhancement in accordance with method 2, and FIG. 7C illustrates spectral enhancement in accordance with method 3. FIGS. 8A-8C illustrate electrical stimulation patterns for the CIS strategy for vowel /a/ sung by a female singer at F0s ranging from C4 (262 Hz) to G4 (392 Hz). FIG. 8A illustrates no enhancement, FIG. 8B illustrates spectral enhancement in accordance with method 2, and FIG. 8C illustrates spectral enhancement in accordance with method 3.

FIG. 9 is a functional block diagram of an example cochlear implant system 950, in accordance with embodiments presented herein. As shown, cochlear implant system 950 comprises one or more microphones 900, a pre-processing module 902, a target fundamental frequency (F0) estimator module 904, a harmonic analyzer module 906, a band-pass filterbank 908, a spectral harmonic enhancement module 910, a post-processing module 912, and an electrical stimulus generation module (stimulator) 914. It is to be appreciated that the specific functional blocks/module shown in FIG. 9 are merely illustrative and that a cochlear implant could include other components that, for ease of description and illustration, have been omitted from FIG. 9.

In the example of FIG. 9, the one or more microphones 900 capture/receive acoustic signals 901. The one or more microphones 900 convert the acoustic signals 901 into electrical signals, which in turn are provided to the pre-processing module 902, the F0 estimator module 904, and the harmonic analyzer module 906. The pre-processing module 902 performs standard pre-processing operations on the acoustic signals 901 and generates pre-filtered output signals 905 that, as described further below, are the basis of further processing operations.

The pre-filtered output signals 905 are provided to the band-pass filterbank 908. The band-pass filterbank 908 uses the pre-filtered output signals 905 to generate a suitable set of bandwidth limited channelized signals 907 that each includes a spectral component of the received acoustic sound signals 901. That is, the band-pass filterbank 908 is a plurality of band-pass filters that separates the pre-filtered output signal 905 into multiple components, each one carrying a single frequency sub-band of the original signal (i.e., frequency components of the received sounds signal as included in pre-filtered output signal 905). The number 'm' of channelized signals 907 generated by the band-pass filterbank 908 may depend on a number of different factors including, but not limited to, implant design, number of active electrodes, coding strategy, and/or recipient preference(s). In certain arrangements, twenty-two (22) channelized signals 907 are created. The channelized signals 907 are provided to the spectral harmonic enhancement module 910.

As noted, the F0 estimator 904 and the harmonic analyzer 906 each receive the acoustic signals 901 from the microphone. Using the acoustic signals 901, the F0 estimator 904 is configured to estimate the target fundamental frequency (F0) of the acoustic signals 901. The F0 estimator 904 provides the estimated F0 909 to each of the harmonic analyzer 906 and the spectral harmonic enhancement module 910. Using the acoustic signals 901, the harmonic analyzer 906 is configured to determine the harmonics of the F0 (as well as any inharmonic components) that are present in the acoustic signals 901. The harmonic analyzer 906 provides the estimated harmonics of the F0 (and inharmonic components) 911 to the spectral harmonic enhancement module 910.

As noted, the channelized signals 907, the estimated F0 909, and the estimated harmonics of F0 911 are provided to the spectral harmonic enhancement module 910. The spectral harmonic enhancement module 910 is configured to use the channelized signals 907, the estimated F0 909, and the estimated harmonics of F0 (and inharmonic components) 911 to perform the spectral harmonic enhancement techniques presented herein. That is, the spectral harmonic enhancement module 910 is configured to apply one of method 1, method 2, or method 3, as described above, to the channelized signals 907 so as to enhance the harmonic components of the acoustic signal 901.

In practice, the spectral harmonic enhancement module 910 applies one of method 1, method 2, or method 3, as described above, to generate "spectral enhanced signals." The spectral harmonic enhancement module 910 also received/obtains "non-enhanced signals" that are generated from the acoustic signal 901. As used herein, non-enhanced signals are signals to which no harmonic enhancement has been applied (e.g., standard processed signals). The spectral harmonic enhancement module 910 mixes the spectral enhanced signals with the non-enhanced signals to generate "spectral harmonic enhanced signals" 913, which are provided to the post-processing module 912. That is, the spectral harmonic enhanced signals 913 are a weighted combination of the spectral enhanced signals and the non-enhanced signals. The mixing ratio of the spectral enhanced signals and the non-enhanced signals can be based, for example on the target fundamental frequency and/or the target harmonic signal-to-noise ratio (or target harmonic signal-to-total signal ratio).

The post-processing module 912 is configured to perform one or more standard processing operations on the spectral harmonic enhanced signals 913. These standard processing operations can include, for example, channelized gain adjustments for hearing loss compensation (e.g., gain adjustments to one or more discrete frequency ranges of the sound signals), noise reduction operations, speech enhancement operations, etc., in one or more of the channels, sound coding, channel mapping (e.g., threshold and comfort level mapping, dynamic range adjustment, volume adjustments, etc.), etc. The processing module 912 generates processed spectral harmonic enhanced signals 915.

The processed spectral harmonic enhanced signals 915 are provided to the electrical stimulus generation module 914. The electrical stimulus generation module 914 generates electrical stimulation signals 916, which are delivered to the recipient. As noted above, FIGS. 4B, 4D, 5B, 5D, 6B, 6D, 7B, 7C, 8B, and 8C illustrate example electrical stimulation signals that can be generated in accordance with certain embodiments presented herein.

It is to be appreciated that the specific functional block/module arrangement shown in FIG. 9 is merely for purposes of illustration. One or more of the various functional modules can could be implemented as part of the same processing block and/or the functional modules can be incorporated in the same or different physical components that could be external to, or implanted in, the body of a recipient. For example, in one arrangement, the one or more microphones 901, the pre-processing module 902, the F0 estimator module 904, the harmonic analyzer module 906, the band-pass filterbank 908, the spectral harmonic enhancement module 910, and the post-processing module 912 could all be external to the recipient, while the electrical stimulus generation module 914 could be implanted in the recipient. In another arrangement, all of the functional modules shown in FIG. 9 could be implanted in the recipient Again, these two arrangements are illustrative and other arrangements are possible.

Current Steering

The above methods are used to enhance the coding of target F0 harmonics at frequency-places in the cochlea which may lie intermediately between electrode sites. However, rather than using sequential stimulation of adjacent electrodes to elicit inter-electrode place-pitch, a method of "current steering" can instead be employed to steer the place of activation. The absolute and relative proportion of electrical current for a virtual channel (e.g., a pair of adjacent electrodes activated simultaneously) can be adjusted to produce an inter-electrode place of excitation in the cochlea which corresponds to the frequency and power/intensity of each target F0 harmonic. In this case, each F0 harmonic is in effect coded by a single (virtual) channel and the lowest F0 (harmonic frequency spacing) that can be coded (resolved) by each channel is therefore limited by the frequency spacing between virtual channels, which for apical channels of the filterbank used in these examples is 125 Hz. Like method 3, the filterbank channel gains (or stimulation levels) are adjusted so that each F0 harmonic is coded by a single channel nearest (quantized) in frequency to the harmonic frequency and at an intensity derived from the total measured harmonic power (see e.g., 303 in FIG. 3). However, the relative intensities applied for example, to a pair of adjacent electrodes which are activated simultaneously (as a virtual channel) to code each harmonic frequency are determined in the same way that stimulus intensities for a pair of adjacent channels are calculated according to the spectral centroid model used in method 2 (see, 203 in FIG. 2). Finally, the cochlear implant system dependent loudness transform (for virtual channels) used to convert filterbank channel magnitudes to electrical current levels (performed in block 914 of FIG. 9) is also applied to determine the specific current levels to apply to each electrode in the virtual channel according to the subject specific electrical dynamic range of each electrode (which may vary across electrodes).

Current Focusing

Place-coding contrast in the neural response can also be enhanced by stimulating channels using "current focusing" (e.g. tripolar, focused multipolar, etc.) which involves simultaneous activation of multiple electrodes. Current focusing is effective in reducing the overlap in stimulation patterns between nearby channels, resulting in a narrower "focused" field of neural excitation. Using current-focused stimulation presented sequentially across channels, method 2 can be used to produce current-focused electrical stimuli which produce a narrower field of excitation in the cochlea for each pair of channels that code a target harmonic. Alternatively, like current steering, the current levels applied to each electrode activated simultaneously in a current-focused stimulus can be determined to provide a more focused inter-electrode place code for each target harmonic. In this case, each F0 harmonic is in effect coded by a single stimulus (channel of information) and the lowest F0 that can be coded is therefore limited by the frequency spacing between current-focused channels/electrodes. The current levels for each simultaneously activated electrode in the focused stimulus, must be determined according to the total power of each harmonic (as per method 3) and the relative ratio (or pattern) of currents needed to steer the place of focused-activation to the target harmonic frequency. This pattern of currents must be determined according to the cochlear implant system dependent transformation used to convert the filterbank channel harmonic power and frequency (as derived from method 3) to electrical current levels for each electrode in the focused stimuli, and the subject specific electrical dynamic range for each electrode (which may vary across electrodes).

Increased Channel Numbers

Increases in frequency/place-coding resolution can also be provided by increasing the number of spectral analysis (filterbank) channels and stimulating channels (electrodes). However, increased spectral resolution in the analysis filterbank comes at the cost of decreased temporal resolution which can adversely affect temporal pitch perception. To supplement decreased temporal resolution, a temporal F0-pitch enhancement technique could be employed with the spectral enhancement techniques presented. As described further below, FIG. 10A, for example, displays an embodiment of the techniques presented herein that includes a combination of temporal and spectral F0 enhancement processes.

Processing in Noise

For all the processing methods described above, the techniques presented herein can improve coding of target harmonic information when presented in competing noise, albeit for harmonic signal-to-noise ratios in which the target harmonic signal can be estimated reliably (e.g., see FIG. 5). For moderate levels of noise where both the spectral and temporal envelope of the target signal are disrupted, the F0 estimator and harmonic analyzer are still capable of providing frequency and power information about target F0 harmonics. As described above, that information can be enhanced in the coded signal (both within and across channels) compared to any non-target (in-harmonic) frequency components.

Combined Spectral and Temporal F0 Enhancement

The techniques presented herein can be used to address the pitch coding limitations of existing cochlear implant systems, discussed above, by providing a system which for example enhances temporal F0 envelope cues to pitch for low F0s, while enhancing spectral F0 harmonic information for higher F0s.

Figure 10A:
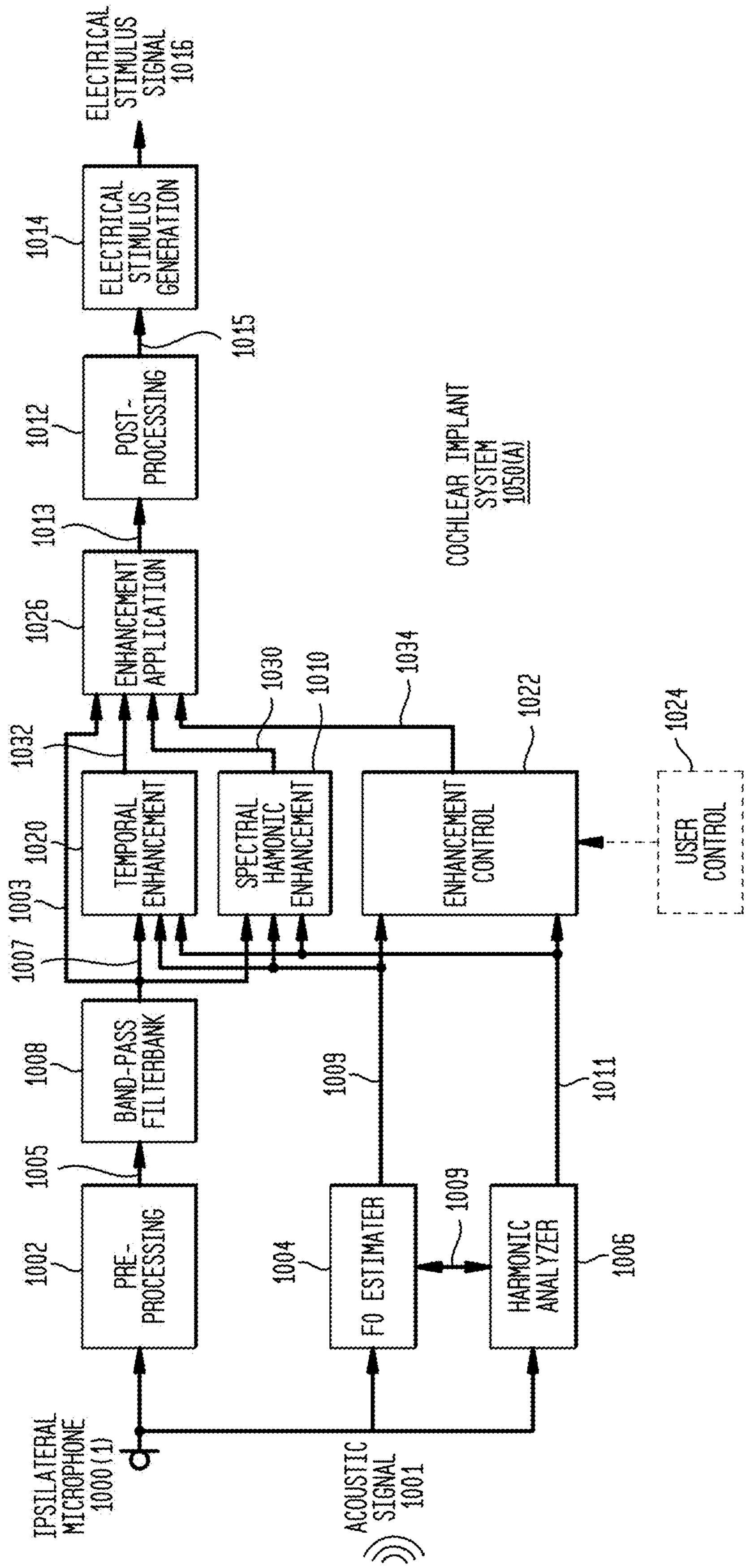
FIG. 10A illustrates an example cochlear implant system configured to implement combined spectral and temporal F0 enhancement, in accordance with embodiments presented herein.

FIG. 10A illustrates an example cochlear implant system 1050(A) configured to implement combined spectral and temporal F0 enhancement, in accordance with embodiments presented herein. Similar to cochlear implant system 950, cochlear implant system 1050(A) comprises one or more microphones 1000(1), a pre-processing module 1002, a target fundamental frequency (F0) estimator module 1004, a harmonic analyzer module 1006, a band-pass filterbank 1008, a spectral harmonic enhancement module 1010, a temporal enhancement module 1020, an enhancement control module 1022, a user control module 1024, an enhancement application module 1026, a post-processing module 1012, and an electrical stimulus generation module 1014. It is to be appreciated that the specific functional blocks/module shown in FIG. 10A are merely illustrative and that a cochlear implant could include other components that, for ease of description and illustration, have been omitted from FIG. 10A.

In the example of FIG. 10A, the one or more microphones 1000 include a microphone 1000(1) (e.g., ipsilateral microphone) that is configured to capture/receive acoustic signal 1001. The microphone 1000(1) convert the acoustic signal 1001 into electrical signals, which in turn are provided to the pre-processing module 1002, the F0 estimator module 1004, and the harmonic analyzer module 1006. The pre-processing module 1002 performs standard pre-processing operations on the acoustic signal 1001 and generates pre-filtered output signals 1005 that, as described further below, are the basis of further processing operations.

The pre-filtered output signals 1005 are provided to the band-pass filterbank 1008. The band-pass filterbank 1008 uses the pre-filtered output signals 1005 to generate a suitable set of bandwidth limited channelized signals 1007 that each includes a spectral component of the received acoustic sound signal 1001. That is, the band-pass filterbank 1008 is a plurality of band-pass filters that separates the pre-filtered output signal 1005 into multiple components, each one carrying a single frequency sub-band of the original signal (i.e., frequency components of the received sounds signal as included in pre-filtered output signal 1005). The number 'm' of channelized signals 1007 generated by the band-pass filterbank 1008 may depend on a number of different factors including, but not limited to, implant design, number of active electrodes, coding strategy, and/or recipient preference(s). In certain arrangements, twenty-two (22) channelized signals 1007 are created. The channelized signals 1007 are provided to the spectral harmonic enhancement module 1010, the temporal enhancement module 1020, and the enhancement application module 1026.

As noted, the F0 estimator 1004 and the harmonic analyzer 1006 each receive the acoustic signal 1001. Using the acoustic signal 1001, the F0 estimator 1004 is configured to estimate the target fundamental frequency (F0) of the acoustic signal 1001. The F0 estimator 1004 provides the estimated F0 1009 to each of the harmonic analyzer 1006, the spectral harmonic enhancement module 1010, the temporal enhancement module 1020, and the enhancement control 1022.

Using the acoustic signal 1001, the harmonic analyzer 1006 is configured to determine the harmonics of the F0 (and inharmonic components) that are present in the acoustic signal 1001. The harmonic analyzer 1006 provides the estimated harmonics (and inharmonic components) 1011 of the F0 to the spectral harmonic enhancement module 1010, the temporal enhancement module 1020, and the enhancement control 1022.

As noted, the channelized signals 1007, the estimated F0 1009, and the estimated harmonics of F0 1011 are provided to the spectral harmonic enhancement module 1010. In this example, the spectral harmonic enhancement module 1010 is configured to use the channelized signals 1007, the estimated F0 1009, and the estimated harmonics of F0 1011 to generate spectral enhanced signals 1030 in accordance with one of method 1, method 2, or method 3, as described above (e.g., in this example, the spectral enhanced signals 1030 are provided to the enhancement application module 1026).

Also as noted above, the channelized signals 1007, the estimated F0 1009, and the estimated harmonics of F0 1011 are provided to the temporal enhancement module 1020. In this example, the temporal enhancement module 1020 configured to use the channelized signals 1007, the estimated F0 1009, and the estimated harmonics of F0 1011 to generate temporal enhanced signals 1032 that provided to the enhancement application module 1026. That is, the temporal enhancement module 1020 is configured to apply a time-varying modulation of the stimulation signal amplitudes and/or adjust pulse rates so as to increase the salience and accuracy of coded F0 rate-pitch information. For example, the temporal enhancement module could apply F0 modulation to the amplitude of channel signals which code each harmonic of the target F0 derived from the harmonic analyzer 1006. Alternatively, or in addition, it could be used to encode each harmonic frequency using stimulation pulse-rate and/or or according to existing temporal F0 enhancement strategies such as OPAL (eTone), F0-Mod, PDT, or FSP.

In addition, also as noted above, the estimated F0 1009 and the estimated harmonics of F0 1011 are provided to the enhancement control module 1022. The enhancement control module 1022, which is configured to receive inputs from the user control module 1024 and is generally configured to dictate/control how the spectral enhanced signals 1030 and the temporal enhanced signals 1032 are mixed with non-enhanced signals 1003 within the enhancement application block 1026. (e.g., a mixer control). The enhancement control module 1022 generates a control signal 1034 that is provided to the enhancement application module 1026.

More specifically, in the example of FIG. 10A, the enhancement application module 1026 is configured to mix the spectral enhanced signals 1030 and/or the temporal enhanced signals 1032 with the non-enhanced signals 1003, under the control of the control signal 1034. As a result, the enhancement application module 1026 generates enhanced signals 1013, which are a weighted combination of the spectral enhanced signals 1030, the temporal enhanced signals 1032, and the non-enhanced signals 1003. The mixing ratio of the signals at enhancement application module 1026 can be controlled, for example, based on the target fundamental frequency, harmonic information, the target harmonic signal-to-noise ratio (or target harmonic signal-to-total signal ratio), etc.

For example, in certain embodiments, the temporal enhancement can be used to increase the salience and accuracy of F0 information coded in the temporal envelope of the stimulus signal. The spectral F0 enhancement can be used to increase the salience and accuracy of F0 harmonic information coded via place of stimulation. The contribution of temporal and spectral enhancement applied by the enhancement application module 1026 to the coded signal is adjusted by the enhancement control block 1024.

Figure 12:
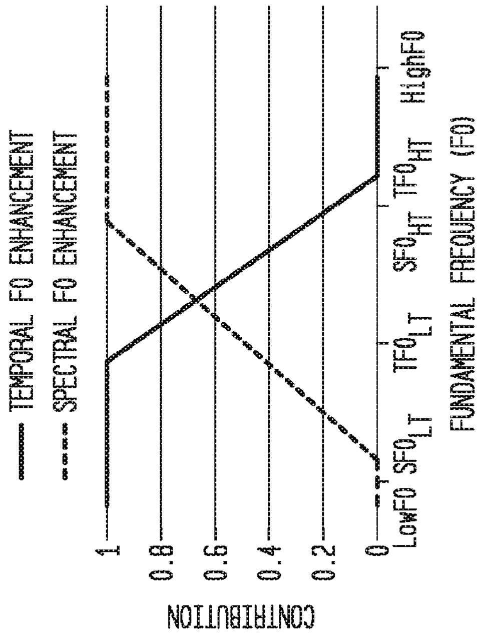
FIGS. 11 and 12 are graphs schematically illustrating combined spectral and temporal F0 enhancement, in accordance with embodiments presented herein.
Figure 11:
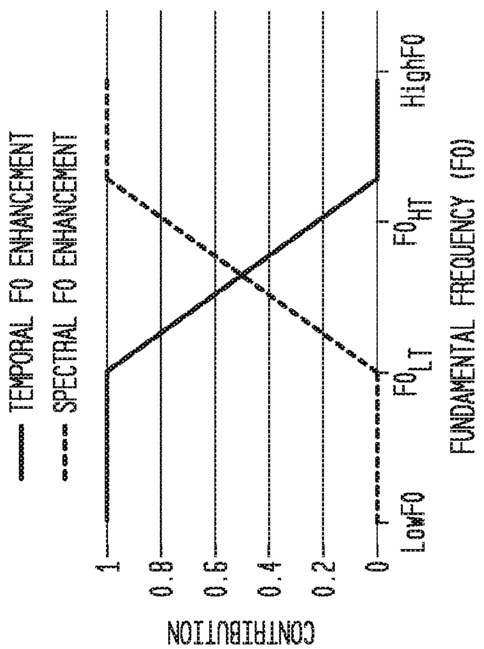

In certain embodiment, and as shown in FIGS. 11 and 12, the enhancement control block 1024 utilizes the target F0 and operates over the continuum of F0s within the voice- and musical-pitch range, denoted as "lowF0" to "highF0." For F0s starting from the lowF0 up to some upper F0 denoted as $F0_{LT}$ the temporal enhancement technique could be utilized exclusively to enhance pitch. Similarly, the spectral F0 enhancement technique could be utilized exclusively to enhance pitch for F0s starting from some F0 denoted as $F0_{HT}$ up to the highF0. For F0s within the F0 transition range spanned by $F0_{LT}$ to $F0_{HT}$ some mixture of the two enhancement techniques could be utilized. The relative contribution of each technique to the coded output could be controlled for example, to smoothly transition between the temporal and spectral techniques in accordance with F0 over the F0 transition range with the temporal technique contributing most for low F0s and the spectral technique contributing most for high F0s (see FIG. 11). An alternative embodiment could utilize independent F0 transition ranges for the two F0 enhancement techniques. For example, the contribution of the temporal F0 enhancement technique could transition across a range of F0s denoted as $TF\mathbf{0}_{LT}$ to $TF\mathbf{0}_{HT}$ while the spectral F0 enhancement technique could transition across a range of F0s denoted as $SF\mathbf{0}_{LT}$ to $SF\mathbf{0}_{HT}$ as depicted in FIG. 12.

The F0 transition range(s) for the temporal and spectral enhancement techniques could be controlled directly by the cochlear implant recipient (user control module 1024 in FIG. 10A). For example, graphical slider controls on a remote control could be used to set the F0 transition range(s) ($TF\mathbf{0}_{LT}$ to $TF\mathbf{0}_{HT}$ and $SF\mathbf{0}_{LT}$ to $SF\mathbf{0}_{HT}$) for the temporal and spectral enhancement techniques, respectively. The magnitude of the temporal and spectral F0 enhancement applied could also be controlled by the user. This feature would allow the system to be tailored to the individual's preferences and their ability to utilize temporal and spectral F0 cues to pitch.

It should however be appreciated that various embodiments presented herein may combine a number of different temporal and spectral F0 enhancement techniques. As such, the embodiments shown in FIGS. 10A, 10B, 11, and 12 are merely illustrative.

Returning to FIG. 10A, as noted above, the enhancement application module 1026 generates enhanced signals 1013, which are provided to the post-processing module 1012. The post-processing module 1012 is configured to perform one or more standard processing operations on the enhanced signals 1013. These standard processing operations can include, for example, channelized gain adjustments for hearing loss compensation (e.g., gain adjustments to one or more discrete frequency ranges of the sound signals), noise reduction operations, speech enhancement operations, etc., in one or more of the channels, sound coding, channel mapping (e.g., threshold and comfort level mapping, dynamic range adjustment, volume adjustments, etc.), etc. The processing module 1012 generates processed enhanced signals 1015.

The processed enhanced signals 1015 are provided to the electrical stimulus generation module 1014. The electrical stimulus generation module 1014 generates electrical stimulation signals 1016, which are delivered to the recipient.

It is to be appreciated that the specific functional block/module arrangement shown in FIG. 10A is merely for purposes of illustration. One or more of the various functional modules can could be implemented as part of the same processing block and/or the functional modules can be incorporated in the same or different physical components that could be external to, or implanted in, the body of a recipient. For example, in one arrangement, the one or more microphones 1001, the pre-processing module 1002, the F0 estimator module 1004, the harmonic analyzer module 1006, the band-pass filterbank 1008, the spectral harmonic enhancement module 1010, and the post-processing module 1012 could all be external to the recipient, while the electrical stimulus generation module 1014 could be implanted in the recipient. In another arrangement, all of the functional modules shown in FIG. 10A could be implanted in the recipient. Again, these two arrangements are illustrative and other arrangements are possible.

Figure 10B:
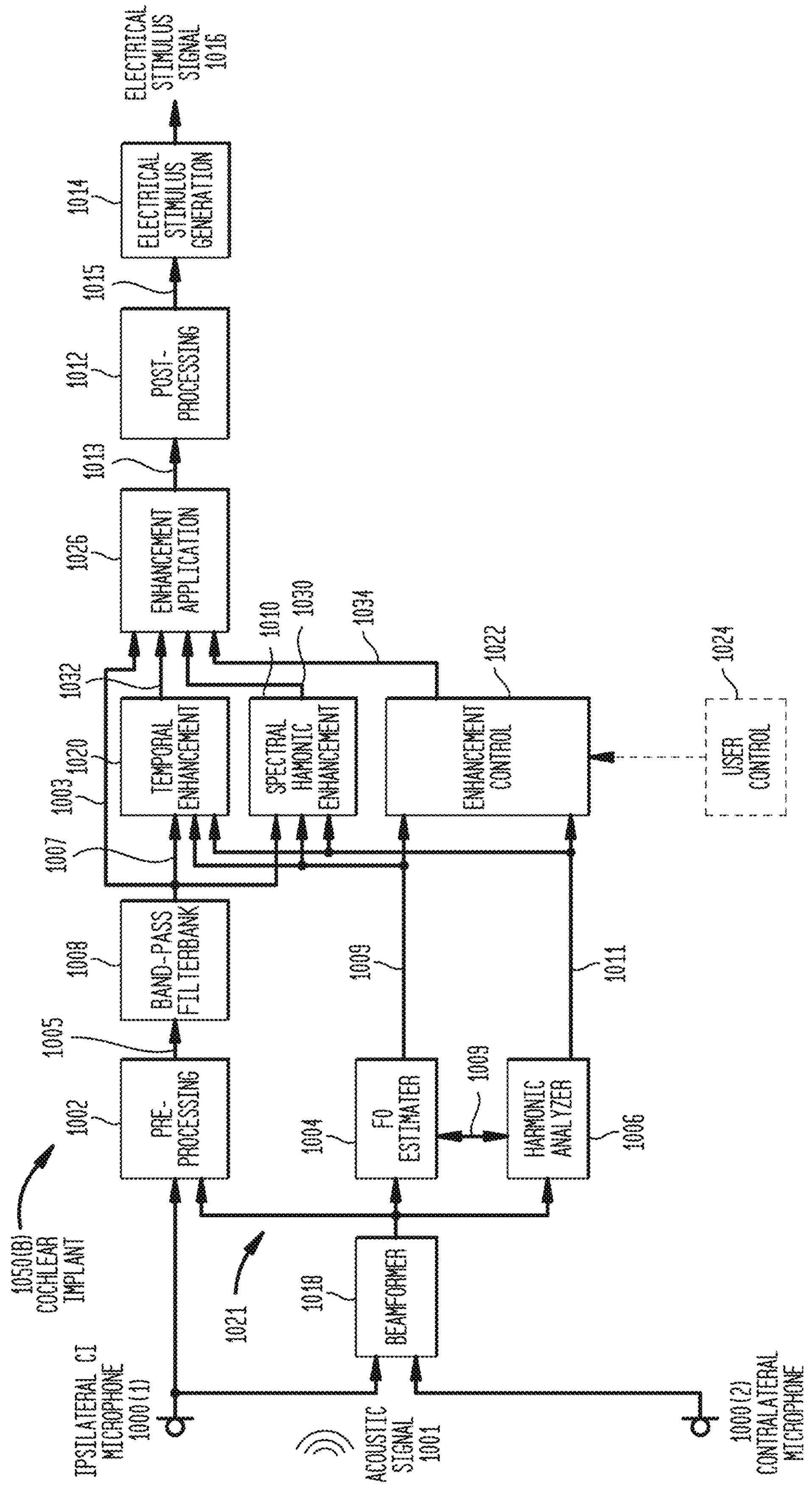
FIG. 10B illustrates another example cochlear implant system configured to implement combined spectral and temporal F0 enhancement, in accordance with embodiments presented herein.

As noted, the specific functional blocks/module shown in FIG. 10A are merely illustrative and that a cochlear implant could include other components. For example, FIG. 10B illustrates a cochlear implant system 1050(B) that is similar to cochlear implant system 1050(A), except that the cochlear implant system 1050(B) includes a second microphone 1000(2) (e.g., contralateral microphone) configured to capture/receive the acoustic signal 1001. As noted, the microphones 1000(1) and 1000(2) convert the acoustic signal 1001 into electrical signals. However, in this example, the acoustic signal 1001 are provided to a beamformer 1018. The beamformer 1018 performs beamforming operations on the acoustic signals 1001 and generates directional signals 1021.

In the example of FIG. 10B, the directional signals 1021 are provided to the pre-processing module 1002, the F0 estimator module 1004, and the harmonic analyzer module 1006. The pre-processing module 1002 performs standard pre-processing operations on the directional signals 1021 and generates pre-filtered output signals 1005 that, as described further below, are the basis of further processing operations.

As noted, the F0 estimator 1004 and the harmonic analyzer 1006 each receive the directional signals 1021. Using the directional signals 1021, the F0 estimator 1004 is configured to estimate the target fundamental frequency (F0) of the acoustic signal 1001. The F0 estimator 1004 provides the estimated F0 1009 to each of the harmonic analyzer 1006, the spectral harmonic enhancement module 1010, the temporal enhancement module 1020, and the enhancement control 1022.

Using the directional signals 1021, the harmonic analyzer 1006 is configured to determine the harmonics of the F0 (and inharmonic components) that are present in the acoustic signal 1001. The harmonic analyzer 1006 provides the estimated harmonics (and inharmonic components) 1011 of the F0 to the spectral harmonic enhancement module 1010, the temporal enhancement module 1020, and the enhancement control 1022. Thereafter, cochlear implant system 1050(B) operates substantially the same as cochlear implant system 1050(A), as described above

Improved F0 Estimation

In certain embodiments, the F0 estimation techniques presented herein are used to track F0 of the most dominant voiced/harmonic signal in the incoming sound, where the most dominant F0 typically corresponds to that of the target talker or sound, at least in quiet condition or in noise when the SNR is not too negative. This process can be improved through use of a multi-microphone beamformer (see FIG. 10B) which can focus the spatial extent of acoustic input to some narrower range (beam) encompassing the target sound location. The use of such beamformers can be used exclusively for input to the F0 estimator irrespective of the spatial input range utilized by the cochlear implant device(s). A further improvement could for example utilize target talker speech tracking algorithms and/or learning neural networks to separate the target speech signal from different talkers and/or background noise.

Acoustic F0 Harmonic Enhancement

Figure 13:
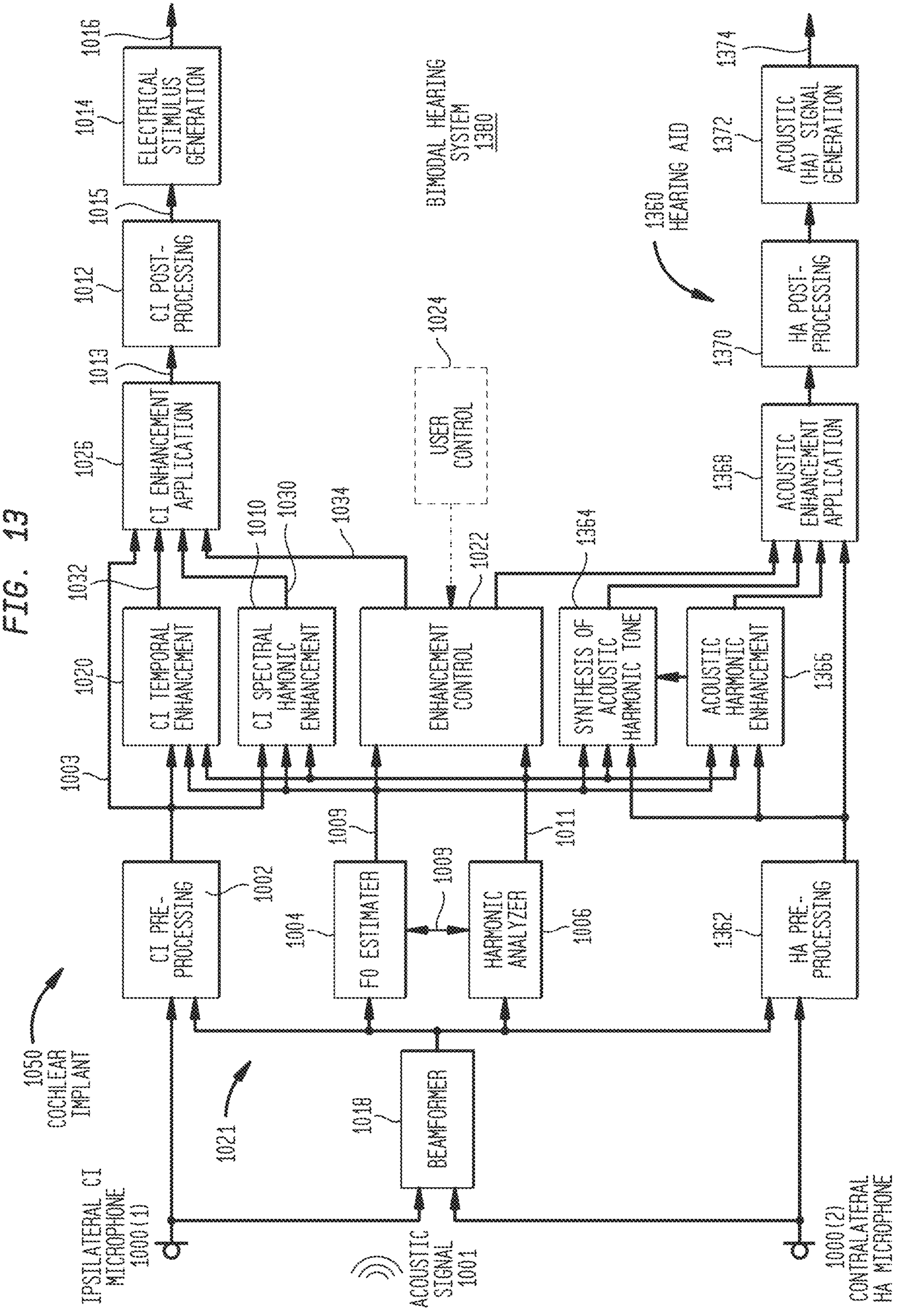
FIG. 13 is functional block diagram of a bimodal hearing system, in accordance with certain embodiments presented herein.

Certain aspects of the techniques presented herein have applicability to electric-acoustic stimulation (EAS) in bimodal and/or hybrid systems which comprise a cochlear implant device in one, or both ears, and a hearing aid (HA) in one, or both ears, as shown in FIG. 13. That is, FIG. 13 is functional block diagram of a bimodal or hybrid hearing system, in accordance with certain embodiments presented herein. For ease of description, FIG. 13 is described as a bimodal hearing system 1380 comprising the cochlear implant system 1050(B) of FIG. 10B, which operates substantially as described above, and a hearing aid 1360. Again, for ease of description, operations of the blocks/modules of cochlear implant system 1050(B) are not repeated with reference to FIG. 13.

The hearing aid 1360 comprises a pre-processing module 1362, an acoustic tone synthesis module 1364, an acoustic harmonic enhancement module 1366, an enhancement application module 1368, a post-processing module 1370, and an acoustic stimulus generation module 1372, which outputs acoustic stimulus signals 1374. It is to be appreciated that the specific functional blocks/module shown in FIG. 13 are merely illustrative and that a combined cochlear implant and hearing aid system could include other components that, for ease of description and illustration, have been omitted from FIG. 13.

In the examples of FIG. 13, some of the principles described above for cochlear implant processing can be applied to the amplified acoustic signal presented by a HA. The aim of this processing it to provide more distinct coding of the target F0 harmonics in the stimulation signal to enhance perception of those harmonics preferential to other signal components in the acoustic signal. For this processing, the "F0 transition range" for the HA device need not be the same as that of the cochlear implant but would be optimized for the hearing range/abilities of the individual. The F0 enhancement technique for the acoustic signal could be based for example, on techniques in which a signal representative of some target F0 is synthesized by 1364 and combined with the pre-processed incoming signal from 1362 to subsequently produce an acoustic signal 1374 delivered to the ear(s). The gains applied to the synthesized and incoming signals could be controlled by the acoustic harmonic enhancement module 1366 to adjust the degree of enhancement applied by the acoustic enhancement application module 1368. The role of the synthesized acoustic signal is to increase the salience of the acoustic pitch percept, particularly when the incoming signal is affected by noise. However, in contrast to various prior art techniques, the synthesized signal could consist of a harmonic-tone having an F0 and harmonic amplitudes modulated to follow that of the target F0 1009 and its harmonic spectrum 1011 (as derived from the methods described in the main body of the invention). Furthermore, the spectral F0 enhancement technique 1366 can be applied to reduce effects of noise in the target F0 harmonic spectrum. The synthesized signal could be combined with the noise reduced target F0 signal instead of, or in addition to, the pre-processed incoming signal. The above acoustic processing techniques may also have applicability to enhancing F0 pitch perception in noise for normal hearing listeners, particularly as real-time F0 processing technology improves.

Figure 15:
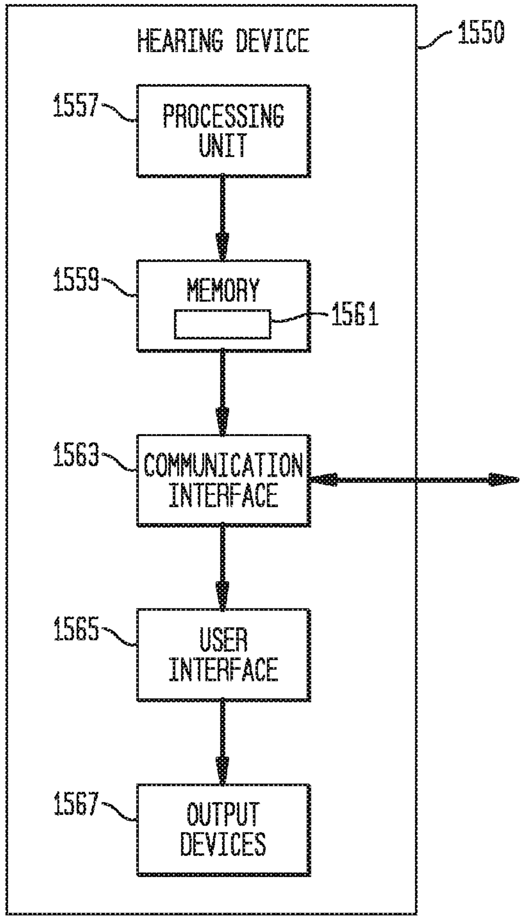
FIG. 15 is schematic block diagram of an example hearing device configured to implement aspects of the techniques presented herein.

FIG. 15 illustrates an example arrangement for a suitable hearing device 1550 (e.g., cochlear implant) configured to implement aspects of the techniques presented herein. In its most basic configuration, the hearing device 1550 includes at least one processing unit 1557 and memory 1559. The processing unit 1557 includes one or more hardware or software processors (e.g., Central Processing Units) that can obtain and execute instructions. The processing unit 1557 can communicate with and control the performance of other components of the hearing device 1550.

The memory 1559 is one or more software or hardware-based computer-readable storage media operable to store information accessible by the processing unit 1557. The memory 1559 can store, among other things, instructions executable by the processing unit 1557 to implement applications or cause performance of operations described herein, as well as other data. The memory 1559 can be volatile memory (e.g., RAM), non-volatile memory (e.g., ROM), or combinations thereof. The memory 1559 can include transitory memory or non-transitory memory. The memory 1559 can also include one or more removable or non-removable storage devices. In examples, the memory 1559 can include RAM, ROM, EEPROM (Electronically-Erasable Programmable Read-Only Memory), flash memory, optical disc storage, magnetic storage, solid state storage, or any other memory media usable to store information for later access. In examples, the memory 1559 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 1559 can include wired media such as a wired network or direct-wired connection, and wireless media such as acoustic, RF, infrared and other wireless media or combinations thereof. In certain embodiments, the memory 1559 comprises enhancement logic 1561 that, when executed, enables the processing unit 1557 to perform aspects of the techniques presented.

In the illustrated example, the hearing device 1550 further includes a communication interface 1563, a user interface 1565, and one or more stimulation output devices 1567 (e.g., one or more of an electrical stimulation generator, an acoustic receiver, etc.).

It is to be appreciated that the arrangement for hearing device 1550 in FIG. 15 is merely illustrative and that aspects of the techniques presented herein may be implemented at a number of different types of systems/devices. For example, the hearing device 1550 can include other components, such as a system bus, component interfaces, a graphics system, a power source (e.g., a battery), among other components.

Figure 16:
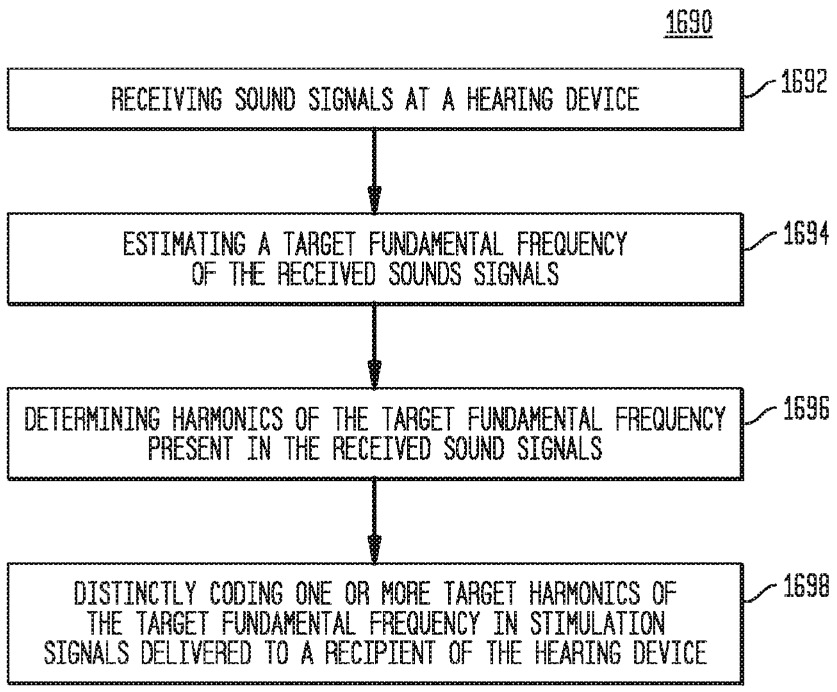
FIG. 16 is a flowchart of an example method, in accordance with certain embodiments presented herein.

FIG. 16 is a flowchart of an example method 1690, in accordance with certain embodiments presented herein. Method 1690 begins at 1692 where a hearing device receives sound signals. At 1694, the hearing device estimates a target fundamental frequency of the received sound signals. At 1696, the hearing device determines harmonics of the target fundamental frequency present in the received sound signals. At 1698, the hearing device distinctly codes one or more target harmonics of the target fundamental frequency in stimulation signals delivered to a recipient of the hearing device.

Figure 17:
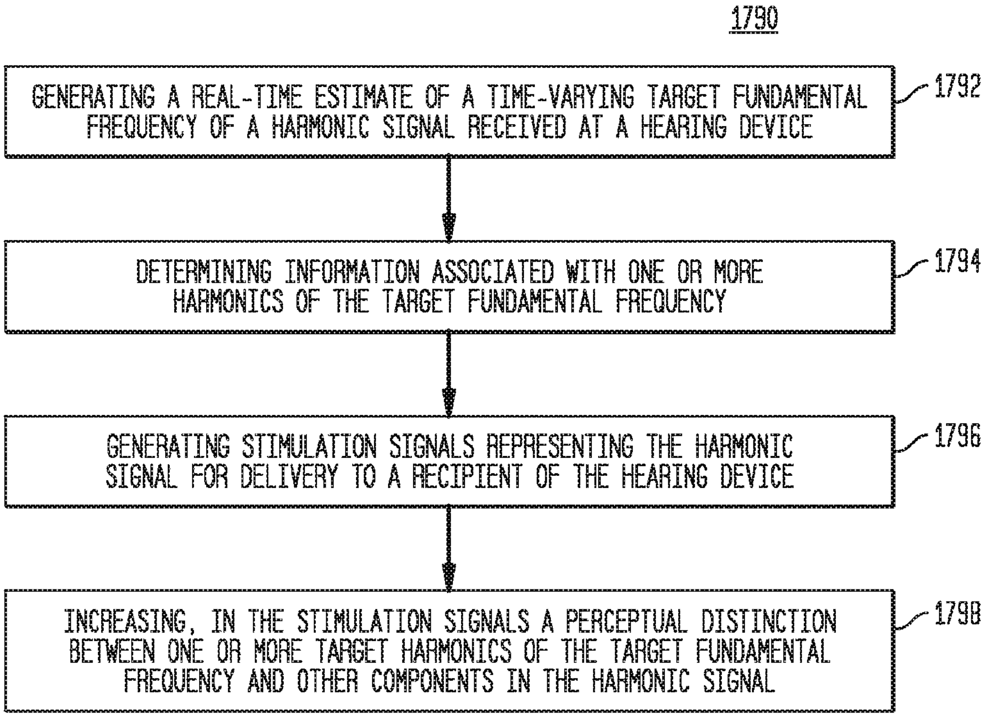
FIG. 17 is a flowchart of another example method, in accordance with certain embodiments presented herein.

FIG. 17 is a flowchart of an example method 1790, in accordance with certain embodiments presented herein. Method 1790 begins at 1792 where a hearing device generates a real-time estimate of a time-varying target fundamental frequency of a harmonic signal received at a hearing device. At 1794, the hearing device determines information associated with one or more harmonics of the target fundamental frequency. At 1796, the hearing device generates stimulation signals representing the harmonic signal for delivery to a recipient of the hearing device. At 1798, the hearing device increases, in the stimulation signals, a perceptual distinction between one or more target harmonics of the target fundamental frequency and other components in the harmonic signal.

Figure 18:
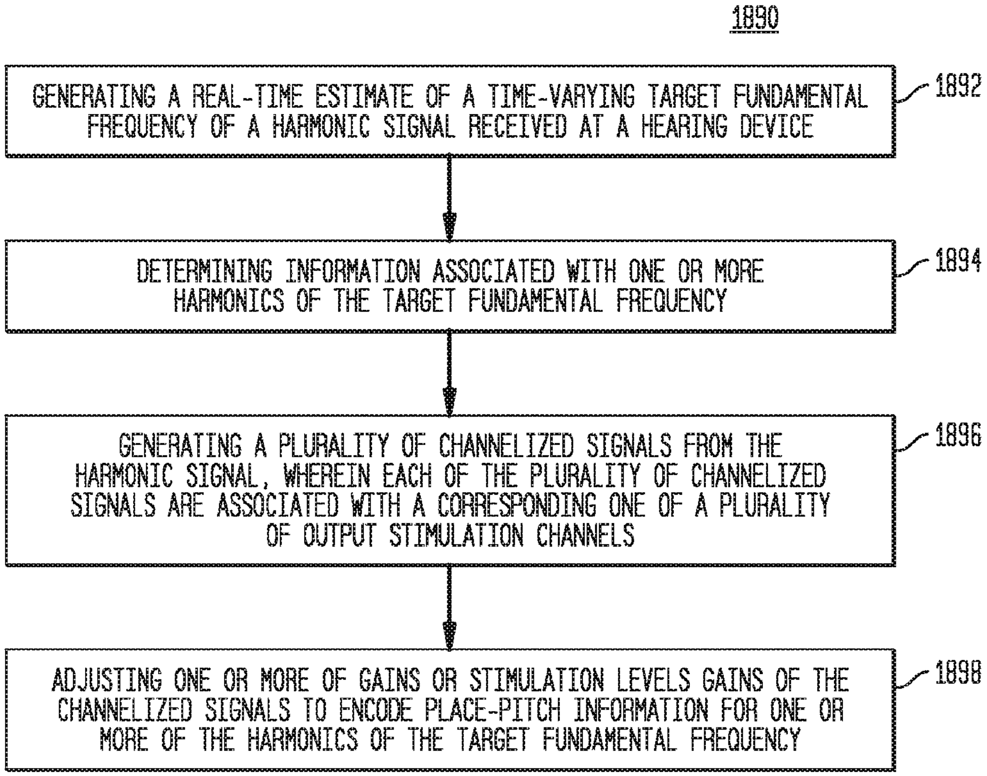
FIG. 18 is a flowchart of another example method, in accordance with certain embodiments presented herein.

FIG. 18 is a flowchart of an example method 1890, in accordance with certain embodiments presented herein. Method 1890 begins at 1892 where a hearing device generates a real-time estimate of a time-varying target fundamental frequency of a harmonic signal received at a hearing device. At 1894, the hearing device determines information associated with one or more harmonics of the target fundamental frequency. At 1896, the hearing device generates a plurality of channelized signals from the harmonic signal, wherein each of the plurality of channelized signals are associated with a corresponding one of a plurality of output stimulation channels. At 1898, the hearing device adjusts one or more of gains or stimulation levels of the channelized signals to encode place-pitch information for one or more of the harmonics of the target fundamental frequency.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A method, comprising:

receiving sound signals at a hearing device;

estimating a target fundamental frequency of the received sound signals;

determining harmonics of the target fundamental frequency present in the received sound signals;

identifying components of the received sound signals that correspond to one or more target harmonics of the target fundamental frequency; and generating stimulation signals for delivery to a recipient of the hearing device, wherein the stimulation signals are configured to enhance perception of the identified components corresponding to the one or more target harmonics relative to a perception of other components of the received sound signals.

2. The method of claim 1, wherein generating the stimulation signals delivered to the recipient comprises:

increasing a relative spectral contrast of the one or more target harmonics relative to other harmonics and non-target information in the received sound signals.

3. The method of claim 1, wherein the hearing device comprises a band-pass filterbank configured to generate a plurality of channelized signals from the received sound signals, wherein each of the plurality of channelized signals are associated with a corresponding one of a plurality of output stimulation channels.

4. The method of claim 3, wherein generating the stimulation signals delivered to the recipient of the hearing device comprises:

adjusting gains or stimulation levels for channelized signals that include relatively more harmonic energy for each of the one or more target harmonics to at least one of pass or amplify the harmonic energy; and reducing the gain or attenuating stimulation levels for channelized signals that carry relatively less or no harmonic energy.

5. The method of claim 3, wherein generating the stimulation signals delivered to the recipient comprises:

generating a power-weighted mean place of stimulation for a pair of adjacent electrical stimulation channels to code frequency and intensity of at least one of the one or more target harmonics.

6. The method of claim 3, wherein generating the stimulation signals delivered to the recipient comprises:

for each of the one or more target harmonics, encoding frequency and intensity information into electrical stimulation signals delivered via only a corresponding pair of adjacent output stimulation channels.

7. The method of claim 6, further comprising:

determining that there is insufficient frequency resolution to distinctly code at least one of the one or more target harmonics using a pair of adjacent output stimulation channels; and in response to determining that there is insufficient frequency resolution, using only a single output stimulation channel to code frequency and intensity information for the at least one of the one or more target harmonics.

8. The method of claim 1, wherein generating the electrical stimulation signals comprises:

generating spectral enhanced signals from the sound signals;

generating non-enhanced signals from the sound signals; and mixing the spectral enhanced signals with the non-enhanced signals according to a mixing ratio determined based on the target fundamental frequency.

9. The method of claim 1, wherein generating the electrical stimulation signals comprises:

generating spectral enhanced signals from the sound signals;

generating temporal enhanced signals from the sound signals;

generating non-enhanced signals from the sound signals; and mixing the spectral enhanced signals with the temporal enhanced signals and the non-enhanced signals according to a mixing ratio determined based on the target fundamental frequency.

10. The method of claim 8, further comprising:

controlling the mixing ratio based on an estimate of how much energy in the received sound signals is related to the target fundamental frequency at different points in time.

11. The method of claim 8, further comprising:

controlling the mixing ratio based on a target harmonic signal power-to-noise power ratio of the received sound signals at different points in time.

12. The method of claim 8, further comprising:

controlling the mixing ratio based on a target harmonic signal power-to-total power ratio for the received sound signals at different points in time.

13. The method of claim 8, further comprising:

controlling the mixing ratio based on an input received from a user of the hearing device.

14. The method of claim 1, wherein generating the stimulation signals comprises:

determining stimulation locations for electrical stimulation signals corresponding to each of the one or more target harmonics to enhance the recipient's perception of the one or more target harmonics preferential to other signal components; and delivering the electrical stimulation signals corresponding to each of the one or more target harmonics at the determined stimulation locations.

15. The method of claim 14, wherein delivering the electrical stimulation signals corresponding to each of the one or more target harmonics at the determined stimulation locations comprises:

delivering each of the stimulation signals using a sequential coding strategy.

16. The method of claim 15, further comprising:

for at least one of the one or more target harmonics, controlling stimulus amplitudes for two sequentially stimulated adjacent channels so that a mean place and intensity of activation for the two sequentially stimulated adjacent channels elicits a percept that corresponds to a frequency and intensity of at least one of the one or more target harmonics.

17. The method of claim 14, wherein delivering the electrical stimulation signals corresponding to each of the one or more target harmonics at the determined stimulation locations comprises:

for at least one of the one or more target harmonics, controlling stimulation levels for two simultaneously stimulated adjacent electrodes so that a mean place and intensity of activation for the two simultaneously stimulated adjacent electrodes elicits a percept that corresponds to a frequency and intensity of the at least one of the one or more target harmonics.

18. The method of claim 14, wherein delivering the electrical stimulation signals corresponding to each of the one or more harmonics at the determined stimulation locations comprises:

for at least one of the one or more target harmonics, controlling stimulation levels for multiple simultaneously stimulated adjacent electrodes to focus a collective stimulation current field to a relatively narrow spatial region that corresponds to the at least one of the one or more target harmonics.

19. The method of claim 14, further comprising:

determining temporal envelope modulations based on the target fundamental frequency; and generating one or more of the electrical stimulation signals in accordance with the temporal envelope modulations.

20. The method of claim 14, further comprising:

using the frequency of the one or more target harmonics to control a stimulation rate for the stimulation signals generated to code the one or more target harmonics.

21. One or more non-transitory computer readable storage media comprising instructions that, when executed by a processor, cause the processor to:

estimate a target fundamental frequency of sound signals received at a hearing device;

determine harmonics of the target fundamental frequency present in the sound signals; and identify components of the received sound signals that correspond to one or more target harmonics of the target fundamental frequency; and determine stimulation signals for delivery to a recipient of the hearing device, wherein the stimulation signals are configured to enhance perception of the identified components corresponding to the one or more target harmonics relative to a perception of other components of the received sound signals.

22. The one or more non-transitory computer readable storage media of claim 21, wherein the instructions operable to determine the stimulation signals comprise instructions operable to:

distinctly place code the one or more target harmonics of the target fundamental frequency into the stimulation signals.

23. The one or more non-transitory computer readable storage media of claim 21, wherein the instructions operable to determine the stimulation signals comprise instructions operable to:

code frequency and intensity information about the one or more target harmonics into the stimulation signals using place of stimulation.

24. The one or more non-transitory computer readable storage media of claim 21, wherein the instructions operable to determine the stimulation signals comprise instructions operable to:

code frequency and intensity information about the one or more target harmonics into the stimulation signals using a weighted combination of place of stimulation and temporal envelope modulations.

25. The one or more non-transitory computer readable storage media of claim 21, wherein the instructions operable to determine the stimulation signals comprise instructions operable to:

code frequency and intensity information about the one or more target harmonics into the stimulation signals using a weighted combination of place of stimulation and rate of stimulation.

26. The one or more non-transitory computer readable storage media of claim 21, wherein the instructions operable to determine the stimulation signals comprise instructions operable to:

code frequency and intensity information about the one or more target harmonics into the stimulation signals using a weighted combination of place of stimulation, rate of stimulation, and temporal envelope modulations.

27. The one or more non-transitory computer readable storage media of claim 26, wherein the weighted combination is determined based on the target fundamental frequency.

28. The one or more non-transitory computer readable storage media of claim 26, wherein the weighted combination is determined based how much of energy in the received sound signals is related to the target fundamental frequency at different points in time.

29. The one or more non-transitory computer readable storage media of claim 26, wherein the weighted combination is determined based on one or more user inputs.

30. The one or more non-transitory computer readable storage media of claim 21, wherein the instructions operable to determine stimulation signals from the sound signals comprise instructions operable to:

increase a relative spectral contrast of the one or more target harmonics relative to non-target information in the sound signals.

31. The one or more non-transitory computer readable storage media of claim 21, wherein the hearing device comprises a band-pass filterbank configured to generate a plurality of channelized signals from the received sound signals, wherein each of the plurality of channelized signals are associated with a corresponding one of a plurality of output stimulation channels.

32. The one or more non-transitory computer readable storage media of claim 21, wherein the instructions operable to determine the stimulation signals comprise instructions operable to:

generate spectral enhanced signals from the sound signals;

generate non-enhanced signals from the sound signals; and mix the spectral enhanced signals with the non-enhanced signals according to a mixing ratio determined based on the target fundamental frequency.

33. The one or more non-transitory computer readable storage media of claim 21, wherein the instructions operable to determine the stimulation signals comprise instructions operable to:

generate spectral enhanced signals from the sound signals;

generate temporal enhanced signals from the sound signals;

generating non-enhanced signals from the sound signals; and mix the spectral enhanced signals with the temporal enhanced signals and the non-enhanced signals according to a mixing ratio determined based on the target fundamental frequency.

34. The one or more non-transitory computer readable storage media of claim 21, wherein the instructions operable to determine the stimulation signals comprise instructions operable to:

determine stimulation locations for the stimulation signals corresponding to each of the one or more target harmonics to enhance the recipient's perception of the one or more target harmonics preferential to other signal components; and deliver the stimulation signals corresponding to each of the one or more target harmonics at the determined stimulation locations.

* * * * *